(12) United States Patent
Gibson et al.

(10) Patent No.: US 9,645,132 B2
(45) Date of Patent: May 9, 2017

(54) STABILISING AND ANALYSING FATTY ACIDS IN A BIOLOGICAL SAMPLE STORED ON SOLID MEDIA

(71) Applicant: ADELAIDE RESEARCH & INNOVATION PTY LTD., Adelaide (AU)

(72) Inventors: Robert Gibson, Port Willunga (AU); Liu Ge, Malvern (AU)

(73) Assignee: ADELAIDE RESEARCH & INNOVATION PTY LTD, Adelaide (AU)

( * ) Notice: Subject to any disclaimer, the term of this patent is extended or adjusted under 35 U.S.C. 154(b) by 271 days.

(21) Appl. No.: 14/371,664

(22) PCT Filed: Jan. 11, 2013

(86) PCT No.: PCT/AU2013/000021
§ 371 (c)(1),
(2) Date: Jul. 10, 2014

(87) PCT Pub. No.: WO2013/104025
PCT Pub. Date: Jul. 18, 2013

(65) Prior Publication Data
US 2015/0027208 A1 Jan. 29, 2015

(51) Int. Cl.
*G01N 33/487* (2006.01)
*A61B 5/15* (2006.01)
(Continued)

(52) U.S. Cl.
CPC .......... *G01N 33/487* (2013.01); *A61B 5/15* (2013.01); *A61B 5/15003* (2013.01);
(Continued)

(58) Field of Classification Search
CPC ..... A61B 5/1405; A61B 5/15; A61B 5/15003; A61B 5/150305; A61B 5/150358;
(Continued)

(56) References Cited

U.S. PATENT DOCUMENTS 3,085,003 A 4/1963 Morris
6,379,318 B1 4/2002 Nishimura et al.
(Continued)

FOREIGN PATENT DOCUMENTS

CN 1170460 A 1/1998
CN 1192648 A 9/1998
(Continued)

OTHER PUBLICATIONS

Micic S., et al., "Improved stability of Apolipoproteins A-I and B in Filter-Paper blood spots impregnated with Ascorbic acid." Clinical Chimica Acta, vol. 5, No. 7 (1995).
(Continued)

*Primary Examiner* — Francis Gray
(74) *Attorney, Agent, or Firm* — McBee Moore Woodward & Vanik IP, LLC

(57) ABSTRACT

The present invention relates to a method for stabilizing fatty acids present in a sample such as bodily fluids. The present invention further relates to a solid medium which is capable of stabilizing fatty acids applied thereto, and a method for preparing same. The present invention further relates to a method for determining the fatty acid composition of a sample.

74 Claims, 8 Drawing Sheets

(51) Int. Cl.
*C11B 5/00* (2006.01)
*C09K 15/22* (2006.01)
*G01N 33/49* (2006.01)
*G01N 33/493* (2006.01)
*G01N 30/88* (2006.01)

(52) U.S. Cl.
CPC .. *A61B 5/150305* (2013.01); *A61B 5/150358* (2013.01); *A61B 5/150755* (2013.01); *C09K 15/22* (2013.01); *C11B 5/00* (2013.01); *C11B 5/0007* (2013.01); *G01N 33/49* (2013.01); *G01N 33/493* (2013.01); *F04C 2270/0421* (2013.01); *G01N 2030/8813* (2013.01)

(58) Field of Classification Search
CPC ..... A61B 5/150755; C09K 15/22; C11B 5/00; C11B 5/0007; G01N 1/36; G01N 2030/8813; G01N 30/50; G01N 33/48; G01N 33/487
See application file for complete search history.

(56) References Cited

U.S. PATENT DOCUMENTS

| | | | | |
|---|---|---|---|---|
| 6,673,763 | B1* | 1/2004 | Hansen | C11D 3/38672 435/188 |
| 7,498,133 | B2* | 3/2009 | Fomovskaia | B01J 20/28023 435/287.2 |
| 2004/0115689 | A1 | 6/2004 | Augello et al. | |
| 2005/0205840 | A1 | 9/2005 | Farneth et al. | |
| 2007/0003621 | A1* | 1/2007 | Nangia | A61K 9/006 424/469 |
| 2013/0115693 | A1* | 5/2013 | Hollander | G01N 1/4005 435/320.1 |
| 2013/0289257 | A1* | 10/2013 | Bales | B01J 20/045 536/23.1 |
| 2015/0004592 | A1* | 1/2015 | van Olphen | C12Q 1/6806 435/5 |

FOREIGN PATENT DOCUMENTS

| | | |
|---|---|---|
| EP | 1 111 384 A1 | 6/2001 |
| JP | 3177658 B2 | 6/2001 |
| JP | 3380230 B2 | 2/2003 |
| JP | 2007-176918 A | 7/2007 |
| WO | 90/03959 A1 | 4/1990 |
| WO | 00/14532 A1 | 3/2000 |
| WO | 00/37602 A1 | 6/2000 |
| WO | 02072870 A2 | 9/2002 |
| WO | 2011/073236 A1 | 6/2011 |

OTHER PUBLICATIONS

Database WPI: XP002742599. Thomas Scientific London (1992).
Ruus V.V. "Manufacture of antioxidant paper" (translated). Rybnoe Khozyaistvo, 1969;44(12):60-61.
Supplemental Partial European Search Report dated Jul. 22, 2015, issued in Application No. 13 73 6428.
Nishio et al., "Brief technical note: A simple method to diagnose adrenoleukodystrophy using a dried blood spot on filter paper." Clinica Chimica Acta, 159 (1986) 77-82 Elsevier.
Bailey-Hall, E. et al., "Validation of a Rapid Measure of Blood PUFA Levels in Humans." Lipids (2008) 43(2), 181-186.

* cited by examiner

STABILISING AND ANALYSING FATTY ACIDS IN A BIOLOGICAL SAMPLE STORED ON SOLID MEDIA

CROSS REFERENCE TO RELATED APPLICATIONS

This application is a §371 National Stage Application of PCT/AU2013/000021, filed Jan. 11, 2013, which claims priority to AU 2012900110, filed Jan. 11, 2012.

BACKGROUND

Field of the Invention

The present invention relates to a method for stabilising fatty acids present in a sample such as bodily fluids. The present invention further relates to a solid medium which is capable of stabilising fatty acids applied thereto, and a method for preparing same. The present invention further relates to a method for determining the fatty acid composition of a sample.

Description of Related Art

A high intake of omega-3 fatty acids especially eicosapentaenoic acid (EPA) and docosahexaenoic acid (DHA) has been associated with reductions in cardiovascular disease, neurodegenerative diseases, diabetes and arthritis in adults and improved mental development in preterm infants. As a result, health authorities around the world are now recommending that intake of omega-3 fatty acids be increased, for example by consuming 2 to 3 meals including fish per week.

Dietary omega-3 fatty acid recommendations for cardiac protection include increasing fish intake to two fatty fish meals per week or consuming 600 or 400 mg/day long chain omega-3 fatty acids respectively for men and women. Although it is known that these recommendations will increase cellular omega-3 fatty acid levels to a level within the cardioprotective range in clinical trials, there is almost no knowledge about how these recommendations are influencing the fatty acid status of the general population. Because the fatty acid status in blood is a useful marker for evaluating cardiac risk in human populations and identifying those individuals who would benefit from dietary omega-3 fatty acid supplementation, evaluation of fatty acid status is important.

Fatty acid profiling of human blood samples which are used as a marker of fatty acid status in human organs has become an important tool for understanding the relationship between dietary fatty acid intake and fatty acid status, since blood levels are thought to reflect biological actions and blood is accessible for collection in human studies. However, conventional approaches to assaying fatty acids in blood involve venous blood collection and an expensive, time consuming multi-step processes that limits its usefulness as a screening tool. Accordingly, a rapid, cheap and reliable means of measuring cellular omega-3 fatty acid levels is necessary.

Until recently, such a rapid and reliable test for the level of omega-3 fatty acids present in human blood (known as The Omega 3 Index) has not been available. In the past few years several companies have advertised a blood spot test in which, following the pricking of a finger, a blood spot is placed on a small piece of filter paper with or without antioxidant(s). After drying, the filter paper is sent to a central laboratory for analysis. It has been claimed that the fatty acids in the blood spot are stable for weeks and that a reliable measure of the Omega 3 Index can be obtained. The present inventors have made attempts to replicate these tests and found that significant degradation of fatty acids occurs over time.

One such product is the Fluka blood collection kit developed by Sigma-Aldrich for the direct assessment of n-3 and n-6 long-chain polyunsaturated fatty acids in blood spots. The only long term stability study to be conducted on blood spot samples collected on Fluka kit papers stored at room temperature showed that there was a significant decline in the long-chain polyunsaturated fatty acid levels (as a percentage of total fatty acids) after 1 month (Min et al. *Prostaglandins, Leukotrienes and Essential Fatty Acids*, 2011 84, 13-18). Thus, the oxidation of long-chain polyunsaturated fatty acids makes this blood spot method impractical for use since it would necessitate that all samples were analysed at a fixed time after collection if results were to be compared.

There is therefore a need for a simple, rapid and reliable method for determining fatty acid content in blood wherein fatty acid degradation during storage of the blood is minimised or eliminated.

Surprisingly, the present inventors have discovered that fatty acids within a dried blood spot may be stabilised for a period of months at ambient conditions. The present inventors have further discovered that a highly accurate determination of the fatty acid composition of blood stored on a solid medium for a period of months may be achieved by stabilising the fatty acids and by controlling contaminants in the solid medium.

SUMMARY

In a first aspect, the present invention provides a method for stabilising fatty acids, the method comprising applying the fatty acids, or a sample comprising the fatty acids, to a solid medium comprising a solid matrix, at least one chelating agent and at least one antioxidant, wherein the solid matrix comprises less than about 2 µg/cm$^2$ of contaminants.

The sample may be a biological sample.

The biological sample may be a bodily fluid, for example blood, saliva, breast milk, urine, semen, blood plasma, synovial fluid, serum and the like.

The bodily fluid may be a mammalian bodily fluid.

The sample may be a fluid comprising the fatty acids, for example a bodily fluid.

The fatty acids may be, or may comprise, unsaturated fatty acids.

The fatty acids may be, or may comprise, long-chain polyunsaturated fatty acids (LCPUFAs).

The fatty acids may be, or may comprise, omega-3 fatty acids, for example EPA, DHA and the like.

In a second aspect the present invention provides a method for determining fatty acid composition of a sample comprising fatty acids, the method comprising:

(a) applying the sample to a solid medium comprising a solid matrix, at least one chelating agent and at least one antioxidant, wherein the solid matrix comprises less than about 2 µg/cm$^2$ of contaminants, such that the sample is sorbed to the solid matrix;

(b) determining the fatty acid composition of the sample sorbed to the solid matrix.

The sample may be a biological sample. In one embodiment the biological sample is a bodily fluid, for example blood, saliva, breast milk, urine, semen, blood plasma, synovial fluid, serum and the like.

The method may comprise determining an amount of one or more classes of fatty acids in the sample as a proportion of total lipids in the sample, or as a proportion of total fatty acids in the sample.

The sample may be applied to the solid medium in an amount that is less than about 100 µL, or less than about 50 µL, or less than about 20 µL.

Step (b) may be performed weeks or months after step (a).

The following statements apply to the first and second aspects:

The solid matrix may comprise less than about 1 µg/cm$^2$ of contaminants, or less than about 0.5 µg/cm$^2$ of contaminants.

The contaminants may be saturated fatty acids.

The solid matrix may be paper, a paper-based matrix or a glass-based matrix.

The paper-based matrix may be silica-gel loaded paper.

The glass-based matrix may be a glass microfiber filter.

The at least one chelating agent may be ethylenediaminetetraacetic acid (EDTA), ascorbic acid, or salts thereof, or citric acid, or salts thereof.

The at least one antioxidant may be butylated hydroxytoluene (BHT), butylated hydroxyanisole (BHA) or t-butylhydroquinone.

Any combinations of the above noted chelating agents and antioxidants are contemplated.

In one embodiment, the chelating agent is ascorbic acid and/or EDTA and the antioxidant is BHT.

The solid medium may be in the form of a strip.

The strip may have dimensions of about 1 cm×3 cm.

The antioxidant(s) may be present on the solid medium in an amount between about 0.001 mg and about 10 mg, or in an amount between about 0.01 mg and about 5 mg, or in an amount between about 0.01 and about 1 mg, or in an amount between about 0.01 mg and about 0.5 mg. In one embodiment the antioxidant(s) is/are present in an amount of about 0.1 mg.

The chelating agent(s) may be present on the solid medium in an amount between about 0.001 mg and about 10 mg, or in an amount between about 0.01 mg and about 5 mg, or in an amount between about 0.01 mg and about 1 mg, or in an amount between about 0.05 mg and about 0.5 mg. In one embodiment the chelating agent(s) is/are present in an amount of about 0.25 mg. In another embodiment the chelating agent(s) is/are present in an amount of about 0.5 mg.

In an embodiment of the first aspect, the present invention provides a method for stabilising fatty acids, the method comprising applying the fatty acids, or a sample comprising the fatty acids, to a solid medium comprising silica gel-loaded paper, EDTA and/or ascorbic acid and BHT.

In another embodiment of the first aspect, the present invention provides a method for stabilising fatty acids, the method comprising applying the fatty acids, or a sample comprising the fatty acids, to a solid medium comprising a glass microfiber filter, EDTA and/or ascorbic acid and BHT.

In a third aspect the present invention provides a solid medium said medium comprising a solid matrix, at least one chelating agent and at least one antioxidant, wherein the solid matrix comprises less than about 2 µg/cm$^2$ of contaminants.

The solid medium may be for stabilisation of fatty acids and/or for use in determining the fatty acid composition of a sample.

The fatty acids may be, or may comprise, unsaturated fatty acids.

The fatty acids may be, or may comprise, LCPUFAs.

The fatty acids may be omega-3 fatty acids, for example EPA, DHA and the like.

The solid matrix may comprise less than about 1 µg/cm$^2$ of contaminants, or less than about 0.5 µg/cm$^2$ of contaminants.

The contaminants may be saturated fatty acids.

The solid matrix may be paper, a paper-based matrix or a glass-based matrix.

The paper-based matrix may be silica gel-loaded paper.

The glass-based matrix may be a glass microfiber filter.

The at least one chelating agent may be EDTA, ascorbic acid, or salts thereof, or citric acid, or salts thereof.

The at least one antioxidant may be butylated hydroxytoluene, butylated hydroxyanisole or t-butylhydroquinone.

Any combinations of the above noted chelating agents and antioxidants are contemplated.

In one embodiment, the chelating agent is ascorbic acid and/or EDTA and the antioxidant is BHT.

The solid medium may be in the form of a strip.

The strip may have dimensions of about 1 cm×3 cm.

The antioxidant(s) may be present on the solid medium in an amount between about 0.001 mg and about 10 mg, or in an amount between about 0.01 mg and about 5 mg, or in an amount between about 0.01 mg and about 1 mg, or in an amount between about 0.01 mg and about 0.5 mg. In one embodiment the antioxidant(s) is/are present in an amount of about 0.1 mg.

The chelating agent(s) may be present on the solid medium in an amount between about 0.001 mg and about 10 mg, or in an amount between about 0.01 mg and about 5 mg, or in an amount between about 0.01 mg and about 1 mg, or in an amount between about 0.05 mg and about 0.5 mg. In one embodiment the chelating agent(s) is/are present in an amount of about 0.25 mg.

In an embodiment of the third aspect the present invention provides a solid medium, said medium comprising silica gel-loaded paper, EDTA and/or ascorbic acid, and BHT.

In another embodiment of the third aspect the present invention provides a solid medium said medium comprising a glass microfiber filter, EDTA and/or ascorbic acid, and BHT.

In a fourth aspect the present invention provides a method for preparing a solid medium comprising a solid matrix, at least one chelating agent and at least one antioxidant, said method comprising providing a solid medium comprising a solid matrix and applying to the solid medium the at least one chelating agent and the at least one antioxidant, wherein the solid matrix comprises less than about 2 µg/cm$^2$ of contaminants.

The solid matrix, chelating agent and antioxidant may be as defined in the above aspects.

The solid matrix may comprise less than about 1 µg/cm$^2$ of contaminants, or less than about 0.5 µg/cm$^2$ of contaminants.

The at least one antioxidant and the at least one chelating agent may be applied to the solid medium in the form of a single solution or separate solutions, one solution comprising the at least one antioxidant and one solution comprising the at least one chelating agent.

The solution(s) may comprise alcohol and water, for example ethanol and water.

The concentration of the at least one antioxidant in the solution may be between about 0.1 mg/mL and about 10 mg/mL, or between about 0.5 mg/mL and about 5 mg/mL.

The concentration of the at least one chelating agent in the solution may be between about 1 mg/mL and about 10 mg/mL, or between about 0.5 mg/mL and about 5 mg/mL.

The solid medium may be in the form of a strip.

The amount of solution applied to the strip may be between about 1 and 500 µL, or between about 1 and 100 µL.

The strip may have dimensions of about 1 cm×3 cm.

The contaminants may be saturated fatty acids.

In a fifth aspect the present invention provides a kit comprising the solid medium of the third aspect.

The kit may be for use in stabilisation of fatty acids and/or for use in determining the fatty acid composition of a sample.

The kit may further comprise a sharp object for obtaining a sample comprising fatty acids from a subject, for example a bodily fluid such as blood.

BRIEF DESCRIPTION OF THE FIGURES

A preferred embodiment of the present invention will now be described, by way of example only, with reference to the accompanying drawings wherein.

DETAILED DESCRIPTION OF A PREFERRED EMBODIMENT

Figure 1:
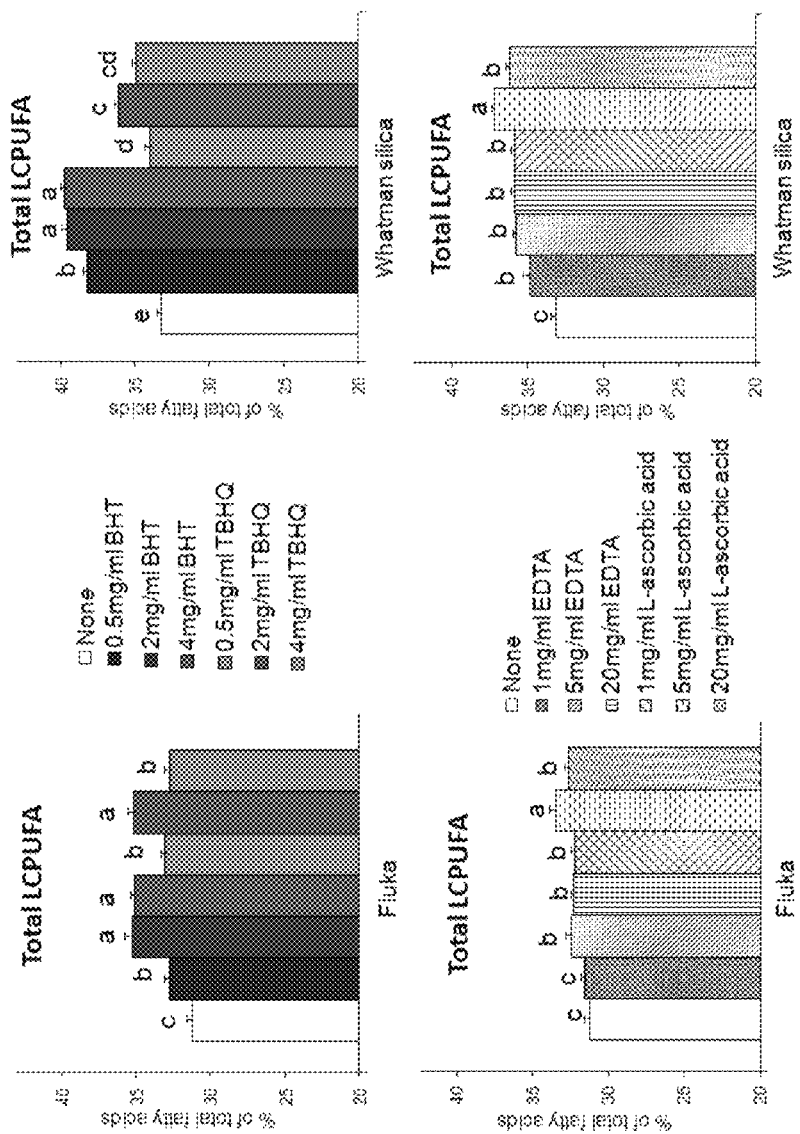
FIG. 1 shows the level of LCPUFA retained in blood spots collected on two types of paper pre-treated with different single antioxidants or iron chelators after 4 weeks storage.

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the term "about" is understood to refer to a range of numbers that a person of skill in the art would consider equivalent to the recited value in the context of achieving the same function or result.

In the context of this specification, the terms "a" and "an" refer to one or to more than one (i.e. to at least one) of the grammatical object of the article. By way of example, "an element" means one element or more than one element.

In the context of this specification, the term "bodily fluid" is understood to include any liquid which originates within a human or animal body, including fluids that are secreted or excreted. Non-limiting examples of bodily fluids include: blood, semen, blood plasma, serum including blood serum, saliva, sweat, urine, breast milk, bile and peritoneal fluid.

In the context of this specification, the term "chelating agent" is understood to include any compound capable of complexing multivalent ions including Group II and Group III multivalent metal ions and transition metal ions.

In the context of this specification, the terms "sorb" and "sorbed" are understood to mean that the relevant entity is absorbed or adsorbed or otherwise incorporated into or onto the solid matrix.

In the context of this specification, the term "biological sample" is understood to mean a sample that is obtained from a living organism, for example plants, animals (including humans), fungi, bacteria, algae and the like.

In the context of this specification, the term "paper-based matrix" is understood to mean a matrix that comprises, includes or contains paper. The paper-based matrix may comprise at least 5% (w/w), at least 10% (w/w), at least 20% (w/w), at least 30% (w/w), at least 40% (w/w), at least 50% (w/w), at least 60% (w/w), at least 70% (w/w), at least 80% (w/w), or at least 90% (w/w), or at least 95% (w/w), or at least 99% (w/w) paper.

In the context of this specification, the term "glass-based matrix" is understood to mean a matrix that comprises, includes or contains glass. The glass-based matrix may comprise at least 5% (w/w), at least 10% (w/w), at least 20% (w/w), at least 30% (w/w), at least 40% (w/w), at least 50% (w/w), at least 60% (w/w), at least 70% (w/w), at least 80% (w/w), or at least 90% (w/w), or at least 95% (w/w), or at least 99% (w/w) glass.

In the context of this specification, the term "cellulose-based matrix" is understood to mean a matrix that comprises, includes or contains cellulose. The cellulose-based matrix may comprise at least 5% (w/w), at least 10% (w/w), at least 20% (w/w), at least 30% (w/w), at least 40% (w/w), at least 50% (w/w), at least 60% (w/w), at least 70% (w/w), at least 80% (w/w), or at least 90% (w/w), or at least 95% (w/w), or at least 99% (w/w) cellulose.

DETAILED DESCRIPTION OF THE INVENTION

The present invention broadly relates to a method for stabilising fatty acids present in a sample, and to a solid medium for use in stabilising fatty acids and for use in determining the fatty acid composition of a sample. The invention also relates to a method for determining the fatty acid composition of a sample comprising fatty acids. The invention further extends to a method for preparing a solid medium for use in stabilising fatty acids and for use in determining the fatty acid composition of a sample.

The method of the first aspect of the invention provides a simple, safe, convenient and reliable means for stabilising fatty acids present in samples. The inventors have found that by use of the method, fatty acids present in blood, breast milk and blood plasma may be stabilised at room temperature for up to 9 weeks with minimal degradation.

The solid medium includes a solid matrix to which is sorbed at least one chelating agent and at least one antioxidant. Solid matrices suitable for use in the present invention include any material that is capable of sorbing the at least one chelating agent, the at least one antioxidant and the fluid. Examples of such matrices include, but are not limited to paper, glass-based matrices, paper-based matrices, cellulose-based matrices, hydrophilic polymers, polytetrafluoroethylene, fibreglass and porous ceramics. In one embodiment the solid matrix is a paper-based matrix, for example silica gel-loaded paper, which includes silica gel-coated paper and silica gel-impregnated paper. Suitable silica gel-loaded papers include those available from Whatman, Inc. under number 3668-915. These papers are comprised of cellulose and large pore silica and have a thickness of about 0.27 mm and a flow rate of about 100 mm per 30 minutes (water). Other non-limiting examples of paper and paper-based matrices include filter paper and chromatography paper.

In an alternative embodiment the solid matrix is a glass-based matrix such as glass wool, or a glass microfiber filter, and in particular a glass microfiber filter comprising or consisting of borosilicate glass. Suitable glass microfiber filters include those available from Whatman Inc. under the numbers A1820-047, B1821-047, C1822-047 and D1823-047.

The present inventors have surprisingly discovered that contaminants present in paper-based solid matrices may interfere with the accurate determination of the amount of the respective classes of fatty acids as a proportion of total lipids, particularly when the volume of fluid applied to the solid matrix is low (i.e. less than about 20 μL). In this context, the term "contaminant" or "contaminants" may be understood to mean a compound or compounds whose presence in the solid matrix would increase or decrease the calculated proportion of a class of fatty acids as a proportion of total lipids in a sample applied to the matrix, as compared to the calculated proportion of a class of fatty acids as a proportion of total lipids in the sample prior to application to the solid matrix. Such contaminants include, for example, saturated fatty acids (such as 16:0 and 18:0), esters of saturated fatty acids, resin acids (such as abietic acid, isopimaric acid, dextropimaric acid and levopimaric acid) and esters of resin acids, which find their way into the paper during production. Whilst it is possible to use a blank solid matrix as a control to correct for contaminants when calculating fatty acid proportions, this adds an additional step to the method and hence reduces efficiency. The inventors have found that accurate determination of the amount of the respective classes of fatty acids as a proportion of total lipids in a fluid can be optimised by ensuring that the contaminants in the solid matrix are less than about 2 $\mu g/cm^2$. Accordingly, in embodiments of the first, second third and fourth aspects the solid matrix comprises contaminants in an amount of less than about 2 $\mu g/cm^2$, or less than about 1.9 $\mu g/cm^2$, or less than about 1.8 $\mu g/cm^2$, or less than about 1.7 $\mu g/cm^2$, or less than about 1.6 $\mu g/cm^2$, or less than about 1.5 $\mu g/cm^2$, or less than about 1.4 $\mu g/cm^2$, or less than about 1.3 $\mu g/cm^2$, or less than about 1.2 $\mu g/cm^2$, or less than about 1.1 $\mu g/cm^2$ or less than about 1 $\mu g/cm^2$, or less than about 0.9 $\mu g/cm^2$, or less than about 0.8 $\mu g/cm^2$, or less than about 0.7 $\mu g/cm^2$, or less than about 0.6 $\mu g/cm^2$, or less than about 0.5 $\mu g/cm^2$, or less than about 0.4 $\mu g/cm^2$, or less than about 0.35 $\mu g/cm^2$, or less than about 0.3 $\mu g/cm^2$, or less than about 0.25 $\mu g/cm^2$, or less than about 0.2 $\mu g/cm^2$, or less than about 0.15 $\mu g/cm^2$, or less than about 0.1 $\mu g/cm^2$, or less than or equal to about 0.15 $\mu g/cm^2$, or less than or equal to about 0.12 $\mu g/cm^2$. Alternatively, the solid matrix may comprise contaminants in an amount between about 0.005 $\mu g/cm^2$ and about 0.5 $\mu g/cm^2$, or in an amount between about 0.005 $\mu g/cm^2$ and about 0.3 $\mu g/cm^2$, or in an amount between about 0.005 $\mu g/cm^2$ and about 0.1 $\mu g/cm^2$, or in an amount between about 0.005 $\mu g/cm^2$ and about 0.2 $\mu g/cm^2$, or in an amount between about 0.005 $\mu g/cm^2$ and about 0.15 $\mu g/cm^2$. In alternative embodiments of the first, second, third or fourth aspects, prior to application of the fatty acids, or sample comprising the fatty acids, the solid matrix comprises saturated fatty acids and/or resin acids, in an amount of less than about 2 $\mu g/cm^2$, or less than about 1.9 $\mu g/cm^2$, or less than about 1.8 $\mu g/cm^2$, or less than about 1.7 $\mu g/cm^2$, or less than about 1.6 $\mu g/cm^2$, or less than about 1.5 $\mu g/cm^2$, or less than about 1.4 $\mu g/cm^2$, or less than about 1.3 $\mu g/cm^2$, or less than about 1.2 $\mu g/cm^2$, or less than about 1.1 $\mu g/cm^2$ or less than about 1 $\mu g/cm^2$, or less than about 0.9 $\mu g/cm^2$, or less than about 0.8 $\mu g/cm^2$, or less than about 0.7 $\mu g/cm^2$, or less than about 0.6 $\mu g/cm^2$, or less than about 0.5 $\mu g/cm^2$, or less than about 0.4 $\mu g/cm^2$, or less than about 0.3 $\mu g/cm^2$, or less than about 0.25 $\mu g/cm^2$, or less than about 0.2 $\mu g/cm^2$, or less than about 0.15 $\mu g/cm^2$, or less than about 0.1 $\mu g/cm^2$, or less than or equal to about 0.15 $\mu g/cm^2$, or less than or equal to about 0.12 $\mu g/cm^2$, or prior to application of the fatty acids, or sample comprising the fatty acids, the solid matrix comprises saturated fatty acids and/or resin acids in an amount between about 0.005 $\mu g/cm^2$ and about 0.5 $\mu g/cm^2$, or in an amount between about 0.005 $\mu g/cm^2$ and about 0.3 $\mu g/cm^2$, or in an amount between about 0.005 $\mu g/cm^2$ and about 0.2 $\mu g/cm^2$, or in an amount between about 0.005 $\mu g/cm^2$ and about 0.1 $\mu g/cm^2$, or in an amount between about 0.005 $\mu g/cm^2$ and about 0.15 $\mu g/cm^2$.

As described in the examples herein, by controlling the amount of contaminants present in the solid matrix and by stabilising fatty acids present in a sample, it is possible to determine the fatty acid composition of the sample weeks or even months after application of the sample to the solid matrix with a very high degree of accuracy. As such, where it is desired to accurately determine the fatty acid content of a sample such as blood for example, an individual may simply prick their finger, place a spot of blood on the solid medium, allow it to dry, and then post it to a central laboratory for analysis. No refrigeration of the solid medium is required, nor is express posting of the sample necessary in view of the extended fatty acid stability on the solid medium. The need for venepuncture is also avoided, as is the need to use a blank collection paper, or some other means as a control to correct for contaminants in the solid medium. Accordingly, in another aspect the present invention relates to a method for determining fatty acid composition of a sample comprising fatty acids, the method comprising:

(a) applying the sample to a solid medium comprising a solid matrix, at least one chelating agent and at least one antioxidant, wherein the solid matrix comprises less than about 2 $\mu g/cm^2$ of contaminants, such that the sample is sorbed to the solid matrix;

(b) determining the fatty acid composition of the sample sorbed to the solid matrix.

Step (b) may be performed by methods well known amongst those skilled in the art, for example by derivatisation of the fatty acids in the dried sorbed sample and analysis of the resulting derivatised compounds by gas chromatography (GC). In one embodiment, the fatty acids in the dried sorbed sample are converted to fatty acid methyl esters by direct transmethylation, for example by heating at 70° C. in a solution of 1% $H_2SO_4$ in methanol for 3 hours. The fatty acid methyl esters are then extracted into an organic solvent (such as heptane) and the heptane containing the fatty acid methyl esters is injected into a gas chromatograph. The identification and quantification of the fatty acid methyl esters may be achieved by comparing the retention times and peak area values of unknown samples to those of commercial lipid standards using the Hewlett-Packard Chemstation data system (see Example 1 herein).

Accordingly, in one embodiment, step (b) comprises:

(i) extracting at least a portion of the sample sorbed to the solid matrix to provide an extract comprising derivatised, for example esterified, fatty acids;

(ii) determining the fatty acid composition of the sample based on amounts of the derivatised fatty acids.

The esterified fatty acids may be $C_1$-$C_6$ alkyl esters, for example methyl esters.

The method may comprise determining an amount of one or more classes of fatty acids (preferably unsaturated fatty acids) in the sample as a proportion (for example a percentage) of total lipids present in the sample, or as a proportion of total fatty acids present in the sample. For example, the method may comprise determining an amount of one or more of the following unsaturated fatty acids: 18:1 n-9, 18:2 n-6, 20:4 n-6, 20:5 n-3, 22:5 n-3 and 22:6 n-3. Step (b) may be performed weeks or months after step (a). For example, step (b) may be performed up to about 12 months, up to about 9 months, up to about 8 months, up to about 7 months, up to about 6 months, up to about 5 months, up to about 4 months, up to about 3 months, up to about 2 months, or up to about 1 month after step (a). In some embodiments, step (b) is performed up to about 12 weeks, up to about 11 weeks, up to about 10 weeks, up to about 9 weeks, up to about 8 weeks, up to about 7 weeks, up to about 6 weeks, up to about 5 weeks, up to about 4 weeks, up to about 3 weeks, up to about 2 weeks, or up to about 1 week after step (a).

In order to further minimise the potential for contamination with hydrophobic compounds which could contribute to inaccuracies in determination of the fatty acid composition, the sample obtained in step (a) is preferably stored in a cellophane bag prior to performance of step (b). Preferably, the sample is stored in a cellophane bag in the dark at ambient temperature.

Typically, the sample is a biological sample however those skilled in the art will recognise that the methods and mediums of the invention are applicable to any sample comprising fatty acids, and in particular unsaturated fatty acids, which are particularly sensitive to degradation. In some embodiments the biological sample is a bodily fluid. Non-limiting examples of bodily fluids include: blood, saliva, breast milk, urine, semen, blood plasma, synovial fluid and serum. In alternative embodiments the sample may be an oil, for example an edible oil such as a marine oil or a vegetable oil, which comprises unsaturated fatty acids for which it is desired to determine the fatty acid composition. It may be desirable to determine the fatty acid composition of such oils for quality control purposes and/or to assess shelf life. In another embodiment the oil may be an oil derived from a genetically engineered crop (such as canola) which has been developed to produce increased amounts of selected fatty acids, for example omega-3 fatty acids, as a proportion of total lipids produced. In this instance the method of the second aspect could be used to quantify the increase in omega-3 fatty acids as a proportion of total lipids produced.

The sample may be applied to the solid medium in an amount that is less than about 100 µL, or less than about 90 µL, or less than about 80 µL, or less than about 70 µL, or less than about 60 µL, or less than about 50 µL, or less than about 40 µL, or less than about 30 µL, or less than about 25 µL, or less than about 20 µL, or about 20 µL.

In other embodiments, the sample may be applied to the solid medium in an amount between about 10 µL and about 250 µL, or between about 10 µL and about 150 µL, or between about 10 µL and about 100 µL, or between about 10 µL and about 75 µL, or between about 10 µL and about 60 µL, or between about 30 µL and about 60 µL, or between about 10 µL and about 20 µL, or between about 10 µL and about 30 µL or about 50 µL.

The solid matrix used in the invention comprises at least one chelating agent which is sorbed thereto. Chelating agents are well known to those skilled in the art. Chelating agents suitable for use in the present invention include, but are not limited to: EDTA, ethyleneglycol-O,O'-bis(2-aminoethyl)-N,N,N',N'-tetraacetic acid (EGTA) triethanolamine, salicyclic acid, diethylenetriaminepentaacetic acid, diethylenetriamine-N,N,N',N',N''-pentaacetic acid, N,N-Bis(2-(bis-(carboxymethyl)amino)ethyl)-glycine, diethylenetriamine pentaacetic acid, [[(Carboxymethyl)imino]bis(ethylenenitrilo)]-tetra-acetic acid, N,N-bis(carboxymethyl)glycine, triglycollamic acid, Trilone A, α,α',α''-trimethylaminetricarboxylic acid, tri(carboxymethyl)amine, aminotriacetic acid, Hampshire NTA acid, nitrilo-2,2',2''-triacetic acid, Titriplex I, Nitrilotriacetic acid and deferoxamine.

The solid matrix used in the invention further comprises at least one antioxidant which is sorbed thereto. Antioxidants suitable for use in the present invention include, but are not limited to: resveratrol, t-butylhydroquinone, BHT, BHA, citric acid, citrate, ascorbic acid, ascorbate, flavanoids such as bacalein, and antioxidant plant extracts.

The antioxidant(s) may be present on the solid medium in an amount between about 0.001 mg and about 10 mg, or in an amount between about 0.01 mg and about 1 mg, or in an amount between about 0.01 mg and about 0.5 mg. In one embodiment the antioxidant(s) is/are present in an amount of about 0.1 mg.

The chelating agent(s) may be present on the solid medium in an amount between about 0.001 mg and about 10 mg, or in an amount between about 0.01 mg and about 1 mg, or in an amount between about 0.05 mg and about 0.5 mg. In one embodiment the chelating agent(s) is/are present in an amount of about 0.25 mg. In another embodiment the chelating agent(s) is/are present in an amount of about 0.5 mg.

The present invention further relates to a method for preparing a solid medium comprising a solid matrix, at least one chelating agent and at least one antioxidant, said method comprising providing a solid medium comprising a solid matrix and applying to the solid medium the at least one chelating agent and the at least one antioxidant, wherein the solid matrix comprises less than about 2 µg/cm² of contaminants.

The solid matrix, chelating agent and antioxidant may be as defined herein. The at least one antioxidant and the at least one chelating agent may be applied to the solid medium in the form of a single solution or separate solutions, one solution comprising the at least one antioxidant and one solution comprising the at least one chelating agent. Alternatively, where the at least one antioxidant and/or the at least one chelating agent are liquids, each may be applied to the solid medium neat.

The solution(s) may comprise an organic solvent and water, for example an alcohol (such as methanol or ethanol) and water.

The concentration of the at least one antioxidant in the solution may be between about 0.1 mg/mL and about 10 mg/mL, or between about 0.5 mg/mL and about 5 mg/mL. The concentration of the at least one chelating agent in the solution may be between about 1 mg/mL and about 10 mg/mL, or between about 0.5 mg/mL and about 5 mg/mL. The amount of solution applied to the strip may be between about 1 and 500 µL, or between about 1 and 100 µL, or about 50 µL. Typically the solution is applied dropwise.

The solid medium may take any shape (for example circular, rectangular, square and the like), but is typically in the form of a strip. The strip may have dimensions between about 1 cm×1 cm and about 1 cm×3 cm, however alternative size strips are contemplated. Typically the solid medium is thin (i.e. between 1 to 2 mm) so as to facilitate cheap and easy posting to a central laboratory in a standard envelope.

The present invention further relates to a kit comprising the solid medium of the third aspect. The kit may further comprise a sharp object (for example a pin, needle or the like) for obtaining a sample comprising fatty acids from a subject, for example a bodily fluid. In one embodiment the bodily fluid is blood. Preferably, the sharp object is pre-sterilised so as to minimise the risk of the subject suffering an infection following the use thereof. The kit may further comprise instructions for use.

EXAMPLES

The invention will now be described in more detail, by way of illustration only, with respect to the following examples. The examples are intended to serve to illustrate this invention and should in no way be construed as limiting the generality of the disclosure of the description throughout this specification.

Example 1

Stabilisation of Blood Spots on Whatman Silica Gel Chromatography Paper Using a Combination of BHT and Ascorbic Acid/EDTA Materials and Methods
Blood Collection Papers Two types of paper were used for blood spot collection: Fluka blood collection kit paper (Sigma-Aldrich, Buchs, Switzerland) and Whatman silica gel chromatography paper (46×57 cm, Whatman, Buckingham, UK). Two commercial phenolic antioxidants, butylated hydroxytoluene and tertiary butylhydroquinone (TBHQ) were purchased from Sigma-Aldrich (St Louis, Mo.). Iron chelation agents, L-ascorbic acid and EDTA were purchased from Chem-supply Company (Gillman, South Australia).

Antioxidant/Chelator (Protectant) Solutions

Fourteen protectant formulations were prepared to stabilize the fatty acids in blood spots on both types of collection paper (Table 1). To determine the optimal antioxidant concentration to control lipid oxidation in the blood spots, both kinds of antioxidants (BHT and TBHQ) at three different concentrations (0.5 mg/ml, 2 mg/ml and 4 mg/ml) were tested (Table 1). L-ascorbic acid and EDTA at levels of 5 mg/ml were used as iron chelators. A drop of each protectant formulation (~50 µl) was spread evenly over collection paper strips and air-dried prior to collection of blood onto the paper.

TABLE 1

Protectant used for treatment of collection papers

| Formulation | Antioxidants | Iron chelators |
|---|---|---|
| 1 | TBHQ 0.5 mg/ml | None |
| 2 | TBHQ 2 mg/ml | None |
| 3 | TBHQ 4 mg/ml | None |
| 4 | BHT 0.5 mg/ml | None |
| 5 | BHT 2 mg/ml | None |
| 6 | BHT 4 mg/ml | None |
| 7 | None | EDTA 1 mg/ml |
| 8 | None | EDTA 5 mg/ml |
| 9 | None | EDTA 20 mg/ml |
| 10 | None | L-ascorbic acid 1 mg/ml |
| 11 | None | L-ascorbic acid 5 mg/ml |
| 12 | None | L-ascorbic acid 20 mg/ml |
| 13 | BHT 2 mg/ml | L-ascorbic acid 5 mg/ml |
| 14 | | EDTA 5 mg/ml |

*Concentrations expressed in mg/ml in 70% ethanol/water solution

Sample Preparation

Blood was collected through the antecubital vein from one healthy volunteer who consumes fish oil regularly and has a very high content of EPA and DHA in blood. Direct transmethylation of the fatty acids in whole blood was achieved by mixing the fresh blood (~50 µl) with 2 ml of 1% (v/v) $H_2SO_4$ (18M AR grade, BDH, Sussex, UK) in anhydrous methanol in a 5 ml sealed vial (Wheaton, Millville, USA) and heating at 70° C. for 3 hrs. The resultant fatty acid methyl esters (FAME) were extracted into heptane and injected into a GC for analysis according to previously established methods (1). Blood spots were obtained by absorbing a drop of fresh blood (~50 µl) on both types of blood collection paper strips (1×3 cm) in the absence or presence of protectant formulations (Table 1) and all blood spots were air dried at ambient temperature for 6 hrs. Once the blood spots were dried, they were divided into 4 groups. The first group was transesterified immediately following the same procedure as for the fresh blood. The results obtained from these samples were compared with those obtained by directly measuring the fatty acid composition of fresh blood to determine whether there was any oxidative loss of LCPUFA in blood spot samples during air drying and provide a baseline measure for fatty acid composition in blood spots. The blood spots in the remaining three groups were stored in cellophane bags in the dark at ambient temperature, and fatty acid composition in these samples were measured at either 2 weeks, 4 weeks or 9 weeks after the time of blood collection. All samples were processed in triplicate.

Gas Chromatography Analysis

FAME were separated and quantified using a GC (Hewlett-Packard 6890; Palo Alto, Calif., USA) equipped with a BPX70 capillary column 50 m×0.32 mm, film thickness 0.25 µm (SGC Pty Ltd., Victoria, Australia), PTV Injector and a flame ionisation detector (FID). The injector temperature was set at 250° C. and the FID temperature at 300° C., a programmed temperature ramp (140-240° C.) was used. Helium gas was utilized as a carrier at a flow rate of 35 cm per second in the column and the inlet split ratio was set at 20:1. The identification and quantification of FAME was achieved by comparing the retention times and peak area values of unknown samples to those of commercial lipid standards (Nu-Chek Prep Inc., Elysian, Minn., USA) using the Hewlett-Packard Chemstation data system.

Statistical Analyses

All statistics analyses were conducted using PASW Statistic 18. Values are expressed as mean±standard deviation (SD). One way ANOVA was used to determine the significant differences between the percentages of fatty acids in total blood lipid after air drying. The effects of paper type and protectant formulation on the changes in fatty acids percentage within the same blood sample over time was tested by using two-way ANOVA. Where significant interactions between paper type and protectant formulation were determined in the ANOVA, changes in fatty acid over time were determined separately for the different paper types one-way ANOVA and Tukey's post-hoc test, $p<0.05$ was accepted as statistically significant.

Results

Effect of Papers and Antioxidant Concentration

In the absence of antioxidants and iron chelators, blood spots collected on Fluka or silica gel papers exhibited a significant decline in the LCPUFA content measured over a 4 week storage period when compared with those blood spots collected on antioxidant pre-treated papers (FIG. 1). Blood spots collected on BHT pre-treated papers retained a higher percentage of LCPUFA than those collected on papers pre-treated with other antioxidant or iron chelators at all three concentrations following 4 weeks of storage at ambient temperature (FIG. 1). The optimal protection afforded by BHT appeared to be at a concentration of 2 mg/ml. It is notable that LCPUFA in blood spots appeared to be more stable on silica gel-coated paper than on Fluka paper.

Effect of Iron Chelators

Spotting blood on both types of paper and allowing the spot to dry for 6 hours resulted in a loss of LCPUFA relative to an equivalent amount of blood transesterified directly in acidified methanol (Tables 2 and 3). Direct transesterification has been demonstrated as a reliable method of determining the fatty acid composition of blood lipids. A significant decline in the percentage of eicosapentaenoic acid (EPA, 20:5n-3) and docosahexaenoic acid (DHA, 22:6n-3) in total blood lipids was also detected for blood spot samples which were collected on papers treated with BHT alone. However, the fatty acid composition measured in blood spots absorbed on either of the collection papers which were pre-treated with a mixture of BHT and either of the iron chelators (L-ascorbic acid or EDTA) were not significantly different from the results obtained from fresh blood (see Table 2 and Table 3). Furthermore, irrespective of the protectant formulations used, blood spots collected on Whatman silica gel paper consistently exhibited a fatty acid composition that was more similar to that in fresh blood compared with blood spots collected on Fluka blood collection kit paper.

TABLE 2

Fatty acid composition (%) of blood spots on Fluka test kit paper determined after air drying for 6 hr compared with results of direct transmethylation of fresh blood

| | Blood spots on Fluka blood collection kit | | | | |
|---|---|---|---|---|---|
| Fatty acid % | Fresh blood | None | BHT 2 mg/ml | BHT 2 mg/ml + L-ascorbic acid 5 mg/ml | BHT 2 mg/ml + EDTA 5 mg/ml |
| 16:0 | *24.24 ± 0.2$^a$ | 27.22 ± 0.16$^d$ | 25.93 ± 0.2$^c$ | 25.02 ± 0.12$^b$ | 25.1 ± 0.1$^b$ |
| 18:0 | 13.83 ± 0.12$^a$ | 15.34 ± 0.12$^d$ | 14.83 ± 0.1$^c$ | 14.23 ± 0.06$^b$ | 14.22 ± 0.07$^b$ |
| 18:1 n-9 | 18.84 ± 0.2$^a$ | 18.25 ± 0.15$^b$ | 18.54 ± 0.23$^{ab}$ | 18.71 ± 0.3$^{ab}$ | 18.72 ± 0.16$^{ab}$ |
| 18:2 n-6 | 19.53 ± 0.13$^a$ | 18.36 ± 0.18$^b$ | 18.93 ± 0.32$^{ab}$ | 19.25 ± 0.16$^a$ | 19.21 ± 0.26$^a$ |
| 20:4 n-6 | 7.52 ± 0.1$^a$ | 6.82 ± 0.12$^c$ | 7.18 ± 0.06$^{bc}$ | 7.27 ± 0.15$^{ab}$ | 7.24 ± 0.05$^{ab}$ |
| 20:5 n-3 | 6.02 ± 0.08$^a$ | 5.55 ± 0.13$^c$ | 5.72 ± 0.11$^b$ | 5.83 ± 0.1$^{ab}$ | 5.85 ± 0.08$^{ab}$ |
| 22:5 n-3 | 3.43 ± 0.05$^a$ | 2.91 ± 0.08$^b$ | 3.03 ± 0.07$^b$ | 3.31 ± 0.06$^a$ | 3.32 ± 0.11$^a$ |
| 22:6 n-3 | 6.58 ± 0.12$^a$ | 5.53 ± 0.15$^c$ | 6.01 ± 0.05$^b$ | 6.38 ± 0.04$^{ab}$ | 6.34 ± 0.06$^{ab}$ |

*Values represent mean ± SD (n = 3), different superscripts indicate significant difference between groups, p < 0.01

TABLE 3

Fatty acid composition (%) of blood spots on Whatman silica gel paper determined after air drying for 6 hr compared with results of direct transmethylation of fresh blood

| | Blood spots on Whatman silica gel paper | | | | |
|---|---|---|---|---|---|
| Fatty acid % | Fresh blood | None | BHT 2 mg/ml | BHT 2 mg/ml + L-ascorbic acid 5 mg/ml | BHT 2 mg/ml + EDTA 5 mg/ml |
| 16:0 | *24.24 ± 0.2$^a$ | 25.92 ± 0.15$^c$ | 25.22 ± 0.12$^b$ | 24.42 ± 0.12$^a$ | 24.30 ± 0.16$^a$ |
| 18:0 | 13.83 ± 0.12$^a$ | 14.98 ± 0.2$^b$ | 14.64 ± 0.17$^b$ | 13.91 ± 0.13$^a$ | 13.92 ± 0.15$^a$ |
| 18:1 n-9 | 18.84 ± 0.2$^a$ | 18.61 ± 0.14$^a$ | 18.62 ± 0.08$^a$ | 18.82 ± 0.15$^a$ | 18.91 ± 0.08$^a$ |
| 18:2 n-6 | 19.53 ± 0.13$^a$ | 18.71 ± 0.2$^b$ | 19.34 ± 0.13$^a$ | 19.44 ± 0.15$^a$ | 19.62 ± 0.2$^a$ |
| 20:4 n-6 | 7.52 ± 0.1$^a$ | 7.13 ± 0.15$^b$ | 7.29 ± 0.11$^{ab}$ | 7.46 ± 0.03$^{ab}$ | 7.54 ± 0.1$^a$ |
| 20:5 n-3 | 6.02 ± 0.08$^a$ | 5.64 ± 0.06$^c$ | 5.80 ± 0.1$^{bc}$ | 5.98 ± 0.07$^{ab}$ | 5.93 ± 0.08$^{ab}$ |
| 22:5 n-3 | 3.43 ± 0.05$^a$ | 3.11 ± 0.1$^b$ | 3.26 ± 0.08$^{ab}$ | 3.42 ± 0.05$^a$ | 3.34 ± 0.08$^{ab}$ |
| 22:6 n-3 | 6.58 ± 0.12$^a$ | 5.86 ± 0.1$^b$ | 6.14 ± 0.1$^b$ | 6.52 ± 0.17$^a$ | 6.5 ± 0.15$^a$ |

*Values represent mean ± SD (n = 3), different superscripts indicate significant difference between groups, p < 0.01

Effect of Long-Term Storage on Blood Spot Fatty Acid Composition

Figure 2:
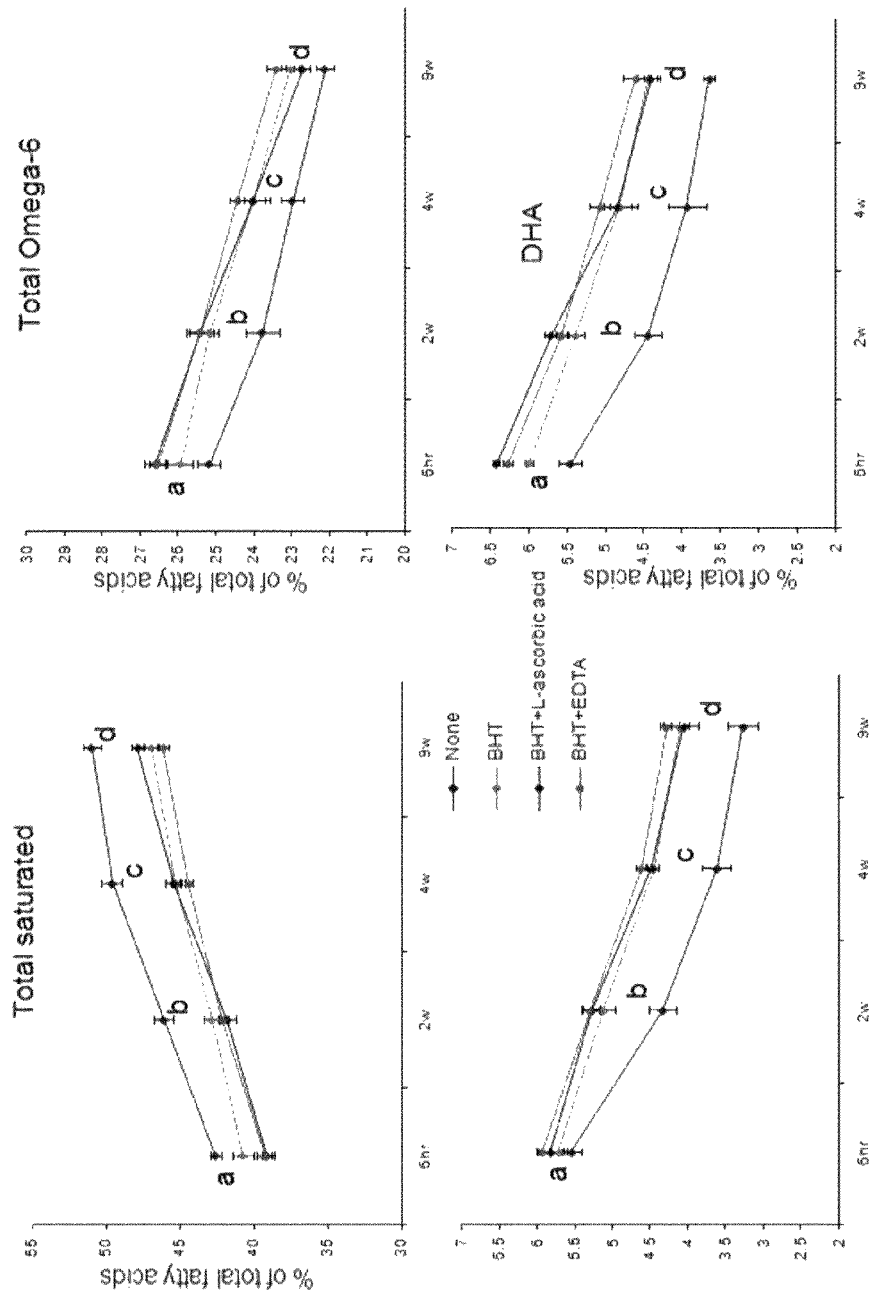
FIG. 2 shows the change in fatty acid composition in blood spots on Fluka test kit during 2 months storage.

Blood spots collected on Fluka test kit paper and stored over a period of 9 weeks showed significantly different fatty acid compositions to those blood spots measured immediately after 6 hrs of air drying (FIG. 2, p<0.01). Irrespective of the protectant formulation used, the levels of omega-6 fatty acids (linolenic acid, LA, 18:2n-6; arachidonic acid, AA, 20:4n-6) and omega-3 EPA and DHA measured in the blood spot collected on Fluka test kit were significantly lower than values measured at base-line as early as 2 weeks after storage and levels continued to decline over the 9 week storage period. Conversely, the percentage of total saturated fatty acids measured in the blood spots increased steadily across the storage period (FIG. 2).

Figure 3:
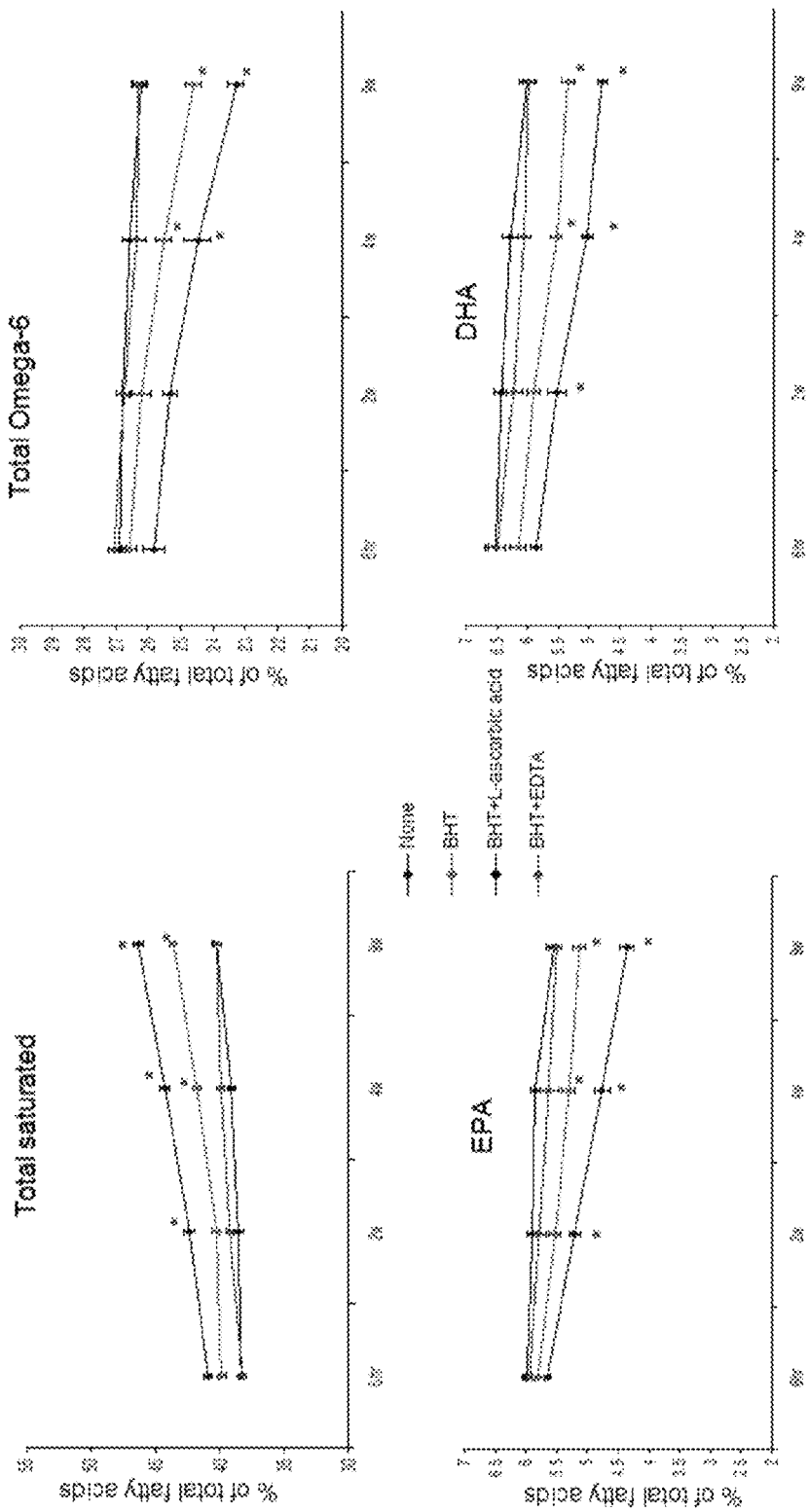
FIG. 3 shows the change in fatty acid composition in blood spots on Whatman silica gel-loaded paper during 2 months' storage.
Figure 4:
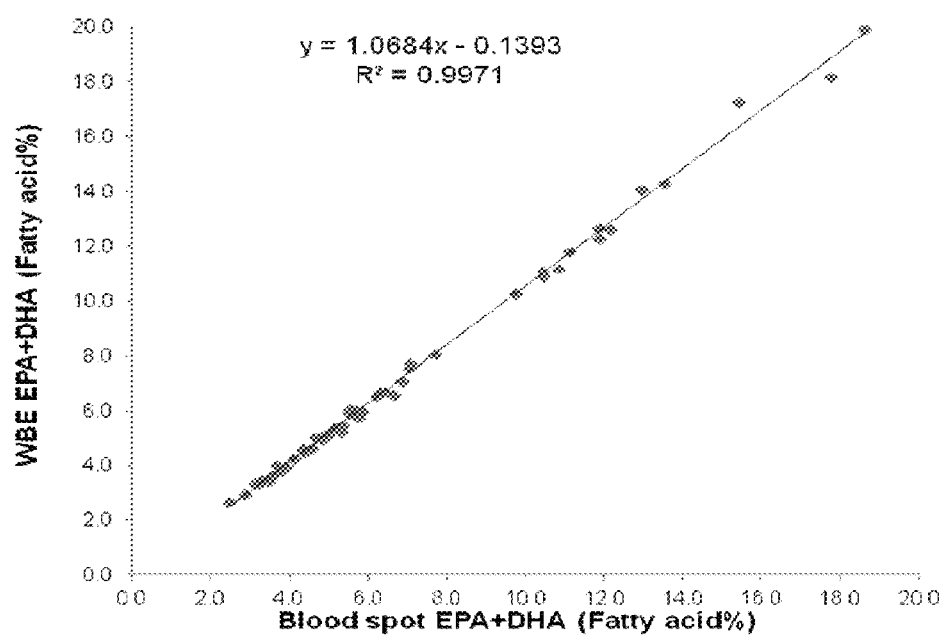
FIG. 4 shows a correlation for EPA+DHA content between capillary dried blood spot (DBS) and whole blood extracted total lipids. EPA+DHA content in DBS (x axis) v. in whole blood extracted total lipids (y axis), whole blood (EPA+DHA) (%)=DBS (EPA+DHA) (%)×1.068−0.139 (r=0.9971, P<0.0001).
Figure 5:
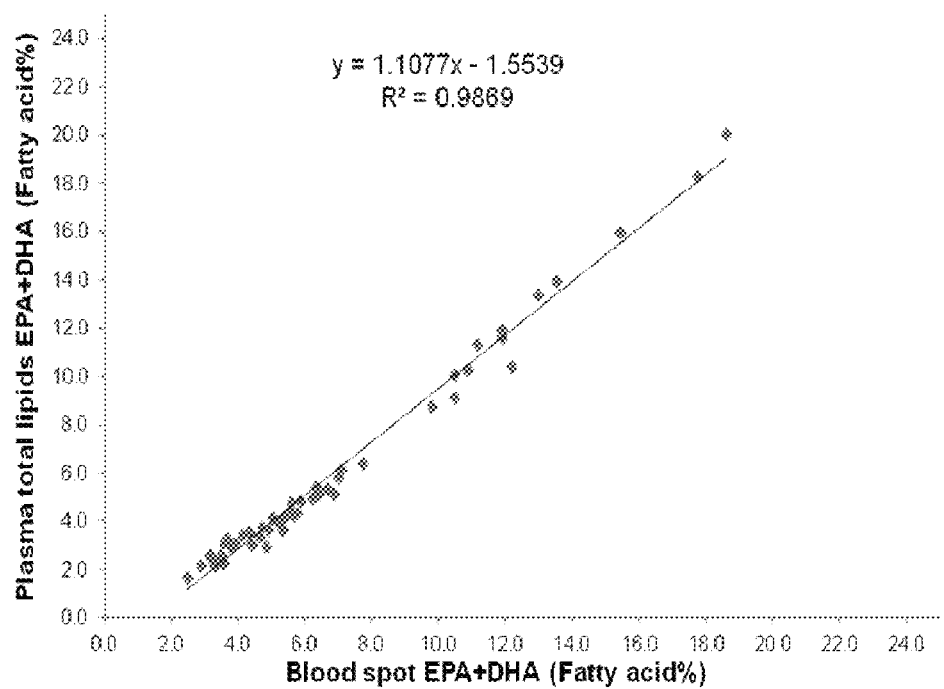
FIG. 5 shows a correlation for EPA+DHA content between capillary dried blood spot and plasma total lipids. EPA+DHA content in DBS (x axis) v. in plasma total lipids (y axis), plasma total lipids (EPA+DHA) (%)=DBS (EPA+DHA) (%)×1.108−1.554 (r=0.9869, P<0.0001).
Figure 6:
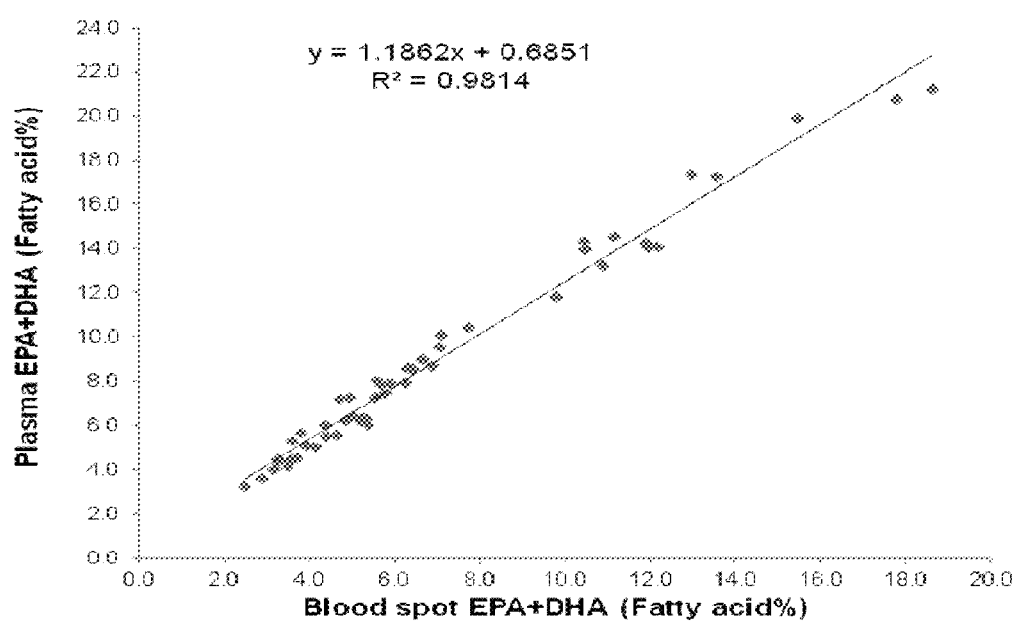
FIG. 6 shows a correlation for EPA+DHA content between capillary dried blood spot and plasma phospholipids. EPA+DHA content in DBS (x axis) v. in plasma phospholipids (y axis), plasma phospholipids (EPA+DHA) (%)=DBS (EPA+DHA) (%)×1.186+0.685 (r=0.9814, P<0.0001).
Figure 7:
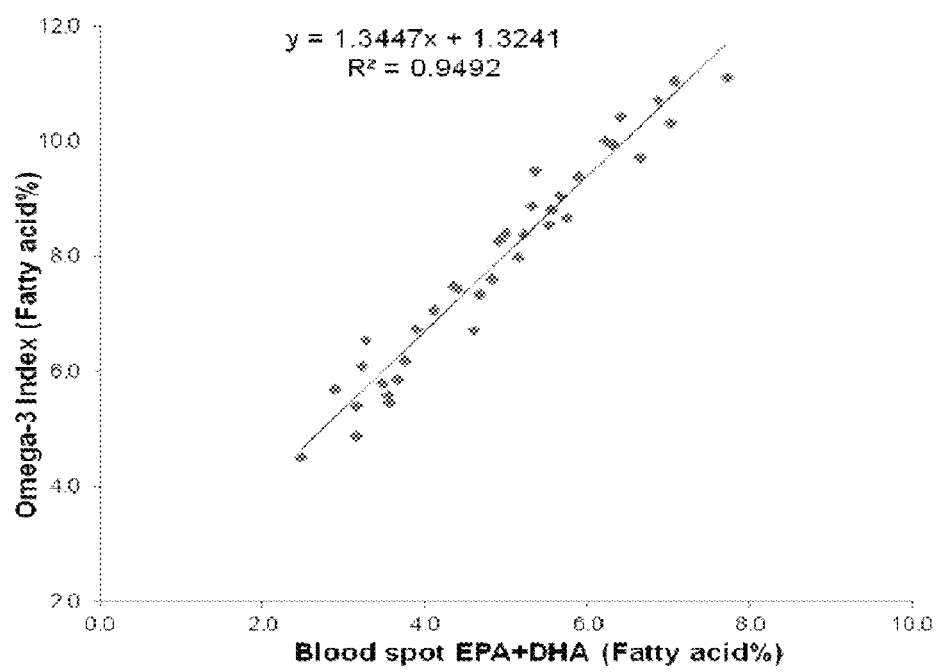
FIG. 7 shows a correlation for level of EPA+DHA between capillary dried blood spot and Omega-3 Index (RBC EPA+DHA) EPA+DHA content in DBS (x axis) v. Omega-3 Index (y axis), Omega-3 Index (%)=Capillary DBS (EPA+DHA) (%)×1.345+1.32 (r=0.9492, P<0.0001).

When blood spots were collected on Whatman silica gel paper without any protectant there were significant declines in the percentage of EPA and DHA in blood spot total lipids after 2 weeks of storage (FIG. 3, p<0.01), however the losses were less than observed on Fluka papers over the same period. By treating the Whatman silica gel papers with BHT, significant reductions in the levels of EPA and DHA were not seen until 4 weeks after storage. Following the addition of both BHT and either of the iron chelators (L-ascorbic acid or EDTA) to the Whatman silica gel paper, the percentage of all LCPUFA in the blood spot samples did not differ significantly from base-line values even after 9 weeks storage at room temperature (FIG. 3).

Discussion

If blood spot technology for evaluation LCPUFA status of individuals is going to be adopted universally, investigators need to be assured that the method is accurate and stable over time. Given that spotting blood on filter paper will naturally expose the LCPUFA in blood to the air, investigators have been concerned about the stability of the LCPUFA in blood spot samples collected in this manner (2). Commercially, blood spot technology is being advertised to consumers inviting them to post in samples on prepared papers to obtain an assessment of their omega 3 index (EPA+DHA). Such a test assumes that the fatty acids in the blood, most notably EPA and DHA, are stable from the time of spotting until the sample is analysed by the distant laboratory. Clearly, if the Fluka test kit is used, a time dependent oxidation of these omega-3 fatty acids will occur regardless of whether the paper is coated with BHT. It has been reported that even with BHT treatment of the collection papers, only about 60% of the n-3 LCPUFA contents in the samples were retained following 1 month storage at ambient temperature (2).

The greatest stability of fatty acid composition in the blood spots was achieved by combining the antioxidant BHT with an iron chelator (L-ascorbic acid or EDTA) and silica gel paper as a collection paper, as this allowed for the maintenance of original EPA and DHA levels in the blood spot after even 2 months of storage at ambient temperature.

In conclusion, the results of this study indicate that a protection system which is made up of a combination of BHT, a chelator and silica gel paper can prevent LCPUFA in blood spots from significant oxidative loss for at least 2 months when stored at ambient temperature. This method has the potential to allow accurate evaluation of fatty acid status in capillary blood samples after long term storage and thus enable comparisons between samples which have been stored for different periods of time.

Example 2

Stabilisation of Blood Plasma Spots on Whatman Silica Gel Chromatography Paper Using a Combination of BHT and EDTA Blood was collected from a subject who regularly consumed one capsule of fish oil per day. The blood sample was centrifuged at 3000 rpm for 10 mins at 4° C. to separate plasma and red blood cells. A drop of plasma (~50 µl) was transesterified directly and the resultant FAME were analysed by GC to provide a baseline for the fatty acid composition in plasma total lipids. The rest of plasma was divided into two portions, the first portion was stored at −20° C., and tested for fatty acid composition by direct transesterification at 1, 2 and 4 weeks. The second portion was spotted onto Whatman silica gel chromatography paper (46×57 cm, Whatman, Buckingham, UK (~50 µl per paper) impregnated with 2 mg/ml BHT and 5 mg/ml EDTA and dried in air for 5-6 hr. The plasma spots were then stored in cellophane bags in the dark at room temperature (19-23° C.), and fatty acid composition in these samples were measured at 1, 2 and 4 weeks after the time of blood collection. All samples were processed in triplicate. The results are shown in Table 4.

TABLE 4

Fatty acid composition of plasma (stored at −20° C.) and plasma spot (stored at room temperature) over 4 weeks storage

| Fatty acids | Plasma $T_0$ (0 hr) | Plasma 1 w | Plasma 2 ws | Plasma 4 ws | Plasma spot 1 w | Plasma spot 2 ws | Plasma spot 4 ws |
|---|---|---|---|---|---|---|---|
| 16:0 | *20.48 ± 0.41 | 20.90 ± 0.23 | 20.84 ± 0.31 | 20.84 ± 0.25 | 21.35 ± 0.36 | 21.24 ± 0.44 | 21.41 ± 0.3 |
| 18:0 | 5.79 ± 0.21 | 5.73 ± 0.07 | 5.66 ± 0.12 | 5.67 ± 0.15 | 5.89 ± 0.19 | 5.94 ± 0.11 | 6.04 ± 0.26 |
| 18:1 n-9 | 27.70 ± 0.52 | 27.60 ± 0.4 | 27.91 ± 0.31 | 28.02 ± 0.26 | 27.61 ± 0.23 | 27.85 ± 0.35 | 27.94 ± 0.28 |
| 18:2 n-6 | 32.44 ± 0.26 | 32.64 ± 0.18 | 32.47 ± 0.44 | 32.49 ± 0.26 | 32.17 ± 0.24 | 32.16 ± 0.25 | 31.83 ± 0.41 |
| 18:3 n-3 | 0.60 ± 0.05 | 0.59 ± 0.03 | 0.59 ± 0.02 | 0.58 ± 0.02 | 0.57 ± 0.03 | 0.58 ± 0.03 | 0.56 ± 0.06 |
| 20:4 n-6 | 6.87 ± 0.13 | 6.87 ± 0.08 | 6.78 ± 0.09 | 6.86 ± 0.06 | 6.71 ± 0.22 | 6.72 ± 0.19 | 6.64 ± 0.16 |
| 20:5 n-3 (EPA) | 1.52 ± 0.06 | 1.53 ± 0.04 | 1.50 ± 0.06 | 1.51 ± 0.04 | 1.46 ± 0.02 | 1.46 ± 0.05 | 1.44 ± 0.04 |

TABLE 4-continued

Fatty acid composition of plasma (stored at −20° C.) and plasma spot (stored at room temperature) over 4 weeks storage

| Fatty acids | Plasma $T_0$ (0 hr) | Plasma | | | Plasma spot | | |
|---|---|---|---|---|---|---|---|
| | | 1 w | 2 ws | 4 ws | 1 w | 2 ws | 4 ws |
| 22:5 n-3 | 0.77 ± 0.03 | 0.77 ± 0.02 | 0.78 ± 0.02 | 0.86 ± 0.03 | 0.79 ± 0.02 | 0.72 ± 0.04 | 0.77 ± 0.04 |
| 22:6 n-3 (DHA) | 3.02 ± 0.12 | 3.04 ± 0.08 | 2.96 ± 0.09 | 3.05 ± 0.06 | 2.98 ± 0.11 | 2.96 ± 0.06 | 2.88 ± 0.08 |

*Data are means ± SD of n = 3 per group. No statistically significant difference between groups. $p < 0.01$ Example 3

Stabilisation of Breast Milk Spots on Whatman Silica Gel Chromatography Paper Using a Combination of BHT and EDTA Breast milk was obtained from a subject who had been lactating for 5 months and was not taking fish oil supplementation. A drop of breast milk (~50 μl) was transesterified directly and the resultant FAME were analysed by GC to provide a baseline for the fatty acid composition in breast milk total lipids. The rest of the breast milk was spotted onto Whatman silica gel chromatography paper (46×57 cm, Whatman, Buckingham, UK (~50 μl per paper) impregnated with 2 mg/ml BHT and 5 mg/ml EDTA, and dried in air for 5-6 hr. Once the breast milk spots were dried, they were divided into 4 groups. The first group was transesterified immediately following the same transesterification procedure as for the fresh breast milk. The results obtained from these samples were compared with those obtained by directly measuring the fatty acid composition of fresh breast milk to determine whether there was any oxidative loss of LCPUFA in breast milk spot samples during air drying and provide a baseline measure for fatty acid composition in breast milk spots. The rest of three groups of breast milk spots were stored in cellophane bags in the dark at room temperature (19-23° C.), and fatty acid composition in these samples were measured at 1, 2 and 4 weeks after the time of breast milk collection. All samples were processed in triplicate. The results are shown in Table 5.

TABLE 5

Fatty acid composition of breast milk spot over 4 weeks storage at room temperature (19-23° C.)

| Fatty acids | Breast milk $t_0$ (0 hr) | Breast milk spot | | | |
|---|---|---|---|---|---|
| | | 5 h | 1 w | 2 ws | 4 ws |
| 16:0 | *30.21 ± 0.18 | 30.22 ± 0.22 | 30.24 ± 0.21 | 30.28 ± 0.12 | 30.26 ± 0.13 |
| 18:0 | 8.14 ± 0.06 | 8.16 ± 0.07 | 8.05 ± 0.06 | 8.20 ± 0.06 | 8.14 ± 0.05 |
| 18:1n-9 | 43.09 ± 0.26 | 43.34 ± 0.22 | 43.31 ± 0.14 | 43.41 ± 0.17 | 43.37 ± 0.13 |
| 18:2n-6 | 15.06 ± 0.09 | 14.87 ± 0.06 | 14.94 ± 0.08 | 14.74 ± 0.10 | 14.84 ± 0.07 |
| 18:3n-3 | 2.10 ± 0.05 | 2.06 ± 0.02 | 2.11 ± 0.03 | 2.03 ± 0.04 | 2.06 ± 0.01 |
| 20:3n-9 | 0.09 ± 0.00 | 0.09 ± 0.00 | 0.09 ± 0.00 | 0.09 ± 0.00 | 0.08 ± 0.00 |
| 20:4n-6 | 0.56 ± 0.01 | 0.54 ± 0.01 | 0.54 ± 0.01 | 0.53 ± 0.02 | 0.54 ± 0.01 |
| 20:5n-3(EPA) | 0.11 ± 0.01 | 0.10 ± 0.01 | 0.11 ± 0.01 | 0.10 ± 0.01 | 0.11 ± 0.01 |
| 22:5n-3 | 0.22 ± 0.01 | 0.22 ± 0.01 | 0.22 ± 0.02 | 0.23 ± 0.01 | 0.22 ± 0.01 |
| 22:5n-3(DHA) | 0.31 ± 0.02 | 0.31 ± 0.02 | 0.30 ± 0.01 | 0.30 ± 0.01 | 0.30 ± 0.01 |

*Data are means ± SD of n = 3 per group. No statistically significant difference between groups, $p < 0.01$ Example 4

Contaminants from Paper and Other Sources

Materials and Methods
Blood Spot Collection Papers
Five types of paper were used as blood spot collection papers, they are two commercially developed blood spot collection papers: Fluka blood collection kit (Sigma-Aldrich, Buchs, Switzerland) and Whatman 903 specimen collection card (Whatman, Buckingham, UK); And three chromatography papers: Whatman 3 MM chromatography paper (46×57 cm, Whatman, Buckingham, UK), Whatman silica gel chromatography paper (46×57 cm, Whatman, Buckingham, UK) and Whatman glass microfiber filter (GF/B 47 mm, Whatman, Buckingham, UK).

Sample Preparation

Approximately 5 ml of blood was collected from one healthy volunteer aged 30 through the antecubital vein and processed immediately after collection. Fresh whole blood (50 µl) was mixed with 2 ml of 1% (v/v) $H_2SO_4$ (18M AR grade, BDH, Sussex, UK) in anhydrous methanol in a 5 ml sealed vial (Wheaton, Millville, USA) and directly transmethylated by heating at 70° C. for 3 hrs. The resultant fatty acid methyl esters (FAME) were extracted into heptane and injected into a GC for analyses according to previously established method (1). At the time of blood collection, two further aliquots of the blood sample (25 µl and 50 µl, respectively) were placed on paper strips (1×1 cm), and processed following the same procedure for the fresh blood. Blank collection paper strips in equivalent area (1×1 cm) without blood were processed by the same procedure as controls. All samples were processed in triplicate.

To evaluate the potential contaminants from sources other than paper during sample collection, processing and storage, blank Whatman glass microfiber filter strips (1×1 cm) were wiped on a 10 $cm^2$ surface area of various materials used in our laboratory including a latex glove, a nitrile glove, a polyethylene (PE) ziplock bag, an aluminium foil ziplock bag or a cellophane bag. The wiped paper samples were then transmethylated by using the method described above and analysed by GC. The contaminant content of blank glass microfiber filter was subtracted from wiped glass microfiber filters to assess the contaminants that originate from those gloves and bags. All the samples were processed in triplicate.

Gas Chromatography Analysis

FAME were separated and quantified by using a GC (Hewlett-Packard 6890; Palo Alto, Calif., USA) equipped with a BPX70 capillary column 50 m×0.32 mm, film thickness 0.25 µm (SGC Pty Ltd., Victoria, Australia), PTV Injector and a flame ionisation detector (FID). The injector temperature was set at 250° C. and the FID temperature at 300° C., a programmed temperature ramp (140-240° C.) was used. Helium gas was utilized as a carrier at a flow rate of 35 cm per second in the column and the inlet split ratio was set at 20:1. The identification and quantification of FAME was achieved by comparing the retention times and peak area values of unknown samples to those of commercial lipid standards (Nu-Chek Prep Inc., Elysian, Minn., USA) using the Hewlett-Packard Chemstation data system.

Statistical Analyses

All statistics analyses were conducted using PASW Statistic 18. Values are expressed as mean± standard deviation (SD). One-way ANOVA was used to determine the significant difference between percentages of fatty acids in total blood lipid, and $p<0.05$ was used to determine statistical significance.

Results and Discussion

Different Results Between Blood Spot Samples and Fresh Blood

When compared with fresh blood measurement, the analysis of 25 µl blood spotted on both silica gel paper and glass microfiber filter produced identical results for fatty acid composition. In contrast, the 25 µl blood spots on the Fluka test kit or Whatman 903 collection card had a significantly lower percentage of omega-3 fatty acids and arachidonic acid (AA, 20:4 n-6) in total blood lipids when compared with the fresh blood measurement (Table 6). This apparent reduction in the proportion of omega-3 and AA in blood spot samples was offset by a significant increase in the percentages of the saturated fatty acids, palmitic acid (16:0) and stearic acid (18:0) measured in these samples. When the volume of blood spot was increased to 50 µl, the fatty acid composition measured from the blood spots collected on Fluka test kit were not significantly different with fresh blood, however, analysis of 50 µl blood spots on the Whatman 903 collection card still produced significantly different fatty acid profile to that in fresh blood (Table 7).

TABLE 6

Fatty acid composition (%) determined in 25 µl dried blood spots compared with fresh blood

| | | Blood spot | | | | |
|---|---|---|---|---|---|---|
| Fatty acid* (%) | Fresh blood 50 µl | Whatman glass microfiber filter 25 µl | Whatman silica gel Paper 25 µl | Whatman 3 MM paper 25 µl | Fluka Test kit 25 µl | Whatman 903 paper 25 µl |
| 16:0 | 22.8 ± 0.4$^a$ | 22.7 ± 0.3$^a$ | 22.9 ± 0.2$^a$ | 23.7 ± 0.1$^b$ | 24.2 ± 0.4$^b$ | 25.2 ± 0.5$^c$ |
| 18:0 | 10.5 ± 0.1$^a$ | 10.6 ± 0.1$^a$ | 10.6 ± 0.2$^a$ | 10.8 ± 0.2$^{ab}$ | 11.2 ± 0.1$^b$ | 11.8 ± 0.2$^c$ |
| 18:1n-9 | 21.2 ± 0.2$^a$ | 21.2 ± 0.1$^a$ | 21.0 ± 0.2$^a$ | 21.0 ± 0.1$^{ab}$ | 20.7 ± 0.3$^b$ | 20.2 ± 0.3$^b$ |
| 18:2n-6 | 24.8 ± 0.3$^a$ | 24.7 ± 0.3$^a$ | 24.8 ± 0.2$^a$ | 24.2 ± 0.1$^b$ | 24.0 ± 0.2$^b$ | 23.5 ± 0.2$^c$ |
| 20:4n-6 | 9.0 ± 0.1$^a$ | 9.1 ± 0.1$^a$ | 9.0 ± 0.1$^a$ | 8.8 ± 0.2$^{ab}$ | 8.5 ± 0.1$^b$ | 8.2 ± 0.2$^c$ |
| 20:5n-3 | 1.30 ± 0.03$^a$ | 1.30 ± 0.02$^a$ | 1.28 ± 0.03$^a$ | 1.22 ± 0.02$^{ab}$ | 1.18 ± 0.02$^b$ | 1.10 ± 0.03$^c$ |
| 22:5n-3 | 1.20 ± 0.02$^a$ | 1.20 ± 0.03$^a$ | 1.20 ± 0.01$^a$ | 1.16 ± 0.03$^{ab}$ | 1.15 ± 0.02$^{ab}$ | 1.10 ± 0.02$^b$ |
| 22:6n-3 | 3.85 ± 0.02$^a$ | 3.83 ± 0.02$^a$ | 3.85 ± 0.03$^a$ | 3.76 ± 0.02$^{ab}$ | 3.68 ± 0.05$^{bc}$ | 3.58 ± 0.06$^c$ |

*Values represent mean ± SD (n = 3), different superscripts indicate significant difference between groups, $p < 0.05$

TABLE 7

Fatty acid composition (%) determined in 50 μl blood spots compared with fresh blood

| Fatty acid* (%) | Fresh blood 50 μl | Blood spot | | | | |
|---|---|---|---|---|---|---|
| | | Whatman glass microfiber filter 50 μl | Whatman silica gel Paper 50 μl | Whatman 3 MM paper 50 μl | Fluka Test kit 50 μl | Whatman 903 paper 50 μl |
| 16:0 | 22.8 ± 0.4$^a$ | 22.9 ± 0.3$^a$ | 23.0 ± 0.2$^a$ | 23.2 ± 0.1$^a$ | 23.6 ± 0.2$^{ab}$ | 24.1 ± 0.2$^b$ |
| 18:0 | 10.5 ± 0.1$^a$ | 10.7 ± 0.1$^a$ | 10.5 ± 0.1$^a$ | 10.7 ± 0.1$^a$ | 10.9 ± 0.2$^{ab}$ | 11.1 ± 0.1$^b$ |
| 18:1n-9 | 21.2 ± 0.2$^a$ | 21.1 ± 0.2$^a$ | 21.2 ± 0.2$^a$ | 21.3 ± 0.1$^a$ | 20.9 ± 0.3$^a$ | 20.2 ± 0.3$^b$ |
| 18:2n-6 | 24.8 ± 0.3$^a$ | 24.6 ± 0.1$^a$ | 24.7 ± 0.2$^a$ | 24.5 ± 0.1$^a$ | 24.4 ± 0.2$^{ab}$ | 24.0 ± 0.3$^b$ |
| 20:4n-6 | 9.0 ± 0.1$^a$ | 9.0 ± 0.2$^a$ | 9.1 ± 0.1$^a$ | 8.8 ± 0.1$^a$ | 8.7 ± 0.2$^{ab}$ | 8.5 ± 0.1$^b$ |
| 20:5n-3 | 1.30 ± 0.03$^a$ | 1.27 ± 0.05$^a$ | 1.28 ± 0.03$^a$ | 1.25 ± 0.03$^a$ | 1.23 ± 0.02$^{ab}$ | 1.16 ± 0.02$^b$ |
| 22:5n-3 | 1.20 ± 0.02$^a$ | 1.25 ± 0.02$^a$ | 1.20 ± 0.05$^a$ | 1.18 ± 0.03$^a$ | 1.16 ± 0.02$^a$ | 1.16 ± 0.03$^a$ |
| 22:6n-3 | 3.85 ± 0.02$^a$ | 3.88 ± 0.02$^a$ | 3.83 ± 0.05$^a$ | 3.82 ± 0.02$^a$ | 3.77 ± 0.06$^{ab}$ | 3.68 ± 0.02$^b$ |

*Values represent mean ± SD (n = 3), different superscripts indicate significant difference between groups, $p < 0.05$ The results presented here clearly demonstrate that the fatty acid status test results from blood spot samples can vary from those obtained from fresh whole blood. The Fluka blood collection kit and Whatman 903 specimen collection card are commercial products which are widely used for blood collection, and Whatman 3 MM chromatography paper is also frequently used as a blood collection paper in clinical trials. However, low volumes of blood (25 μl) on any of these three types of paper produced dubious fatty acid status results when they were used for direct assessment of LCPUFA from a drop of whole blood. From our data it is clear that contaminants from these collection papers interfere with the accurate determination of the amount of the respective classes of fatty acids as a proportion of total lipids. Using blank collection paper as a control to correct for contaminants is feasible for individual fatty acids composition test. However, the variable amount of contaminants from different types of blood collection paper and the possibility that the amount of contaminants present in a same type of paper varies across a sheet or between batches, makes it impractical to apply a correction factor which is based on the contaminants of blank paper with any degree of certainty, especially in large clinical trials.

Contaminants from Different Papers

The inventors have found that the two main contaminants in all types of collection paper corresponded to 16:0 and 18:0 saturated fatty acids (Table 8). This explains the increase in the percentages of 16:0 and 18:0 saturated fatty acids that was detected in blood spot samples when compared with those in fresh blood. Furthermore, the total amount of contaminants varied between different types of collection paper, for example, the Whatman silica gel paper had only 0.1 μg/cm$^2$ of contaminants, whereas some batches of the Whatman 903 paper had nearly 25 times of that amount. Washing the papers with solvents and even treating papers with the transmethylation procedure failed to remove the contaminant, leading us to believe that the fatty acids are constitutive of paper.

Former studies on blood spot tests claimed that no GC peak was observed after processing collection paper alone, however the inventors found contaminant peaks in all types of collection paper tested. It may be the case that small quantities of contaminants in the collection paper may not significantly alter the fatty acid composition test result. For example, Whatman silica gel paper and Whatman glass microfiber filter showed the same result in fatty acid composition with that of fresh blood. However, for those papers which contain high amounts of contaminants such as the Fluka test kit and Whatman 903 sample collection paper, the fatty acid results were obviously different to fresh blood when the volume of blood collected was small. These contaminants may be resin acids or fatty acids, because both are present in wood from which these papers are ultimately synthesised, either as free acids or various esters. Resins and fatty acids from processed water samples obtained from a paper mill, including 16:0 and 18:0 saturated fatty acids have been reported. Thus, it appears that these acids or their esters can remain as impurities in the final paper product and lead to the introduction of contaminants when assessing fatty acid composition of blood spots collected on these papers.

TABLE 8

Amount of contaminants from different types of collection paper during methylation

| Contaminants corresponding to fatty acid peaks* | Whatman glass fibre filter 1.5 × 1.5 cm | Whatman silica gel paper 1.5 × 1.5 cm | Whatman 3 MM paper 1.5 × 1.5 cm | Fluka test kit 1.5 × 1.5 cm | Whatman 903 paper#1 1.5 × 1.5 cm | Whatman 903 paper#2 1.5 × 1.5 cm | Whatman 903 paper#3 1.5 × 1.5 cm |
|---|---|---|---|---|---|---|---|
| 16:0 | 0.1 ± 0.1$^a$ | 0.10 ± 0.05$^a$ | 0.6 ± 0.03$^b$ | 1.2 ± 0.06$^c$ | 1.7 ± 0.1$^d$ | 0.6 ± 0.05$^b$ | 0.12 ± 0.03$^a$ |
| 18:0 | 0.02 ± 0.02$^a$ | 0.03 ± 0.02$^a$ | 0.2 ± 0.03$^b$ | 0.62 ± 0.04$^c$ | 0.71 ± 0.05$^c$ | 0.22 ± 0.02$^b$ | 0.06 ± 0.03$^a$ |
| Total | 0.1 ± 0.1$^a$ | 0.12 ± 0.05$^a$ | 0.8 ± 0.1$^b$ | 1.8 ± 0.1$^c$ | 2.4 ± 0.1$^d$ | 0.82 ± 0.05$^b$ | 0.18 ± 0.03$^a$ |

*The unit for contaminants is μg/cm$^2$ on paper or filter, values represent mean ± SD (n = 3), different superscripts indicate significant difference between groups, $p < 0.05$
1: batch 1;
2: batch 2;
3: batch 3

Potential Contaminants from Other Sources

Sources of contaminants were tested in our laboratory by touching papers to materials including latex gloves, nitrile gloves, PE ziplock bags, aluminum foil ziplock bags and cellophane bags (Table 9). Latex gloves contain a significant amount of contaminants however there was virtually no contamination detected from the nitrile glove. The PE bag and the aluminium bag each contained large amounts of contaminants which corresponded to oleic acid (18:1 n-9) and erucic acid (22:1 n-9), however, the cellophane bag did not result in the appearance of any significant contamination.

a blank value are not effective strategies for removing the contaminants from paper, the choice of a collection paper which contains minimum contaminants is important for the rapid fatty acid composition test. The inventors were unable to detect any significant contaminants for the Whatman silica gel paper and Whatman glass microfiber filter and they showed identical fatty acid composition results with that in fresh blood even when the amount of blood on paper was low (25 µl). Furthermore, the experimental results presented herein also reveal that using nitrile gloves and cellophane bags can prevent blood spot samples from potential contamination during sample collection, processing and storage.

TABLE 9

Amount of potential contaminants from different sources

| Contaminants corresponding to fatty acid peaks* | Nitrile glove | Latex glove | PE ziplock bag | Aluminum foil ziplock bag | Cellophane bag |
| --- | --- | --- | --- | --- | --- |
| 16:0 | 0.005 ± 0.002 | 0.62 ± 0.02 | 0.02 ± 0.01 | 0 | 0 |
| 18:0 | 0 | 0.61 ± 0.01 | 0.01 ± 0.01 | 0 | 0.010 ± 0.002 |
| 18:1 n-9 | 0 | 0 | 0.31 ± 0.02 | 0 | 0 |
| 22:1 n-9 | 0 | 0 | 0.48 ± 0.03 | 0.32 ± 0.02 | 0 |
| Total | 0.005 ± 0.002$^a$ | 1.22 ± 0.02 $^b$ | 0.82 ± 0.05 $^c$ | 0.32 ± 0.02 $^d$ | 0.010 ± 0.002$^a$ |

*The unit for contaminants is µg/cm$^2$ on Whatman glass microfiber filter after wiped on the surface of gloves or bags, values represent mean ± SD (n = 3), different superscripts indicate significant difference between groups, p < 0.05

Latex gloves, PE bags and aluminium bags are widely used in many laboratories. There have been no previous studies focussing on latex gloves as a source of contamination in experiments, with existing investigations reporting only that latex gloves can release endotoxins which may cause an allergy. However, our experiments have indicated that even these widely used laboratory items have the potential to release hydrophobic contaminants and could contribute to alteration in the results of blood fatty acid composition tests, especially when the blood sample volume is low. Thus, to minimize potential contaminant problems from gloves and bags, the use of nitrile gloves and cellophane bags during collection, processing and storage of the blood spot samples is recommended.

In summary, all types of collection papers release contaminants and these contaminants have the potential to alter the results of analyses of dried blood spot samples, particularly when the volume of the blood spot is low. Since either a washing or transmethylating the paper or even subtracting Example 5

Comparison of Capillary Blood Spot and Conventional Measurements of Fatty Acid Status Both capillary and venous blood were collected from 50 subjects. Among all subjects, 35 seldom consumed fish oil supplementation or if they did, consumed only small amounts (<3 ml per day), whereas 15 of them consumed high amounts of fish oil supplementation (~15 ml, MAX-EPA).

A drop of capillary blood (30-50 µl) was absorbed on Whatman silica gel paper impregnated with 2 mg/ml BHT and 5 mg/ml EDTA and dried in air for 5-6 hrs at room temperature (19-23° C.). Once the blood spot samples were dried they were transesterified and the resultant FAME was analysed by GC. For the blood collected by venipuncture, 500 µl of whole blood was extracted by chloroform/isopropanol (2:1, v/v) for total lipids. The remaining blood was centrifuged at 3000 rpm for 10 mins at 4° C. to separate plasma and red blood cells (RBC). Total lipids in plasma and RBC were extracted using chloroform/methanol (2:1, v/v) or chloroform/isopropanol (2:1, v/v) respectively, and the phospholipids fraction was separated from total lipids by thin layer chromatography. The results are shown in Table 10.

TABLE 10

The fatty acid composition from capillary DBS and conventional assays

| Fatty acids | Capillary DBS | Whole blood Total lipids | Plasma Total lipids | Plasma Phospholipids | Red blood cell Phospholipids |
|---|---|---|---|---|---|
| 16:0 | *23.40 ± 1.84$^a$ | 23.61 ± 1.99$^a$ | 23.28 ± 2.47$^a$ | 29.39 ± 1.90$^b$ | 25.36 ± 1.28$^a$ |
| 18:0 | 11.66 ± 1.24$^{ab}$ | 9.90 ± 1.13$^b$ | 7.44 ± 0.94$^c$ | 14.31 ± 1.94$^a$ | 13.67 ± 1.38$^a$ |
| 18:1 n-9 | 18.99 ± 2.84$^b$ | 18.99 ± 2.95$^b$ | 20.78 ± 3.91$^a$ | 10.54 ± 2.51$^d$ | 15.73 ± 1.73$^c$ |
| 18:2 n-6 | 26.71 ± 4.18$^b$ | 27.96 ± 4.64$^b$ | 34.29 ± 5.82$^a$ | 25.37 ± 4.70$^b$ | 14.33 ± 2.82$^c$ |
| 18:3 n-3 | 0.46 ± 0.12$^b$ | 0.48 ± 0.12$^b$ | 0.62 ± 0.15$^a$ | 0.22 ± 0.08$^c$ | 0.17 ± 0.05$^c$ |
| 20:4 n-6 | 9.09 ± 1.60$^b$ | 9.05 ± 1.65$^b$ | 6.46 ± 1.24$^c$ | 9.54 ± 1.95$^b$ | 14.11 ± 2.44$^a$ |
| 20:5 n-3(EPA) | 2.52 ± 2.19$^b$ | 2.78 ± 2.28$^b$ | 2.83 ± 2.20$^b$ | 3.20 ± 2.26$^a$ | 2.65 ± 2.14$^b$ |
| 22:4 n-6 | 0.92 ± 0.33$^b$ | 0.96 ± 0.34$^b$ | 0.17 ± 0.08$^c$ | 0.30 ± 0.2$^c$ | 2.86 ± 0.96$^a$ |
| 22:5 n-3 | 1.78 ± 0.46$^b$ | 1.76 ± 0.52$^b$ | 0.82 ± 0.32$^c$ | 1.41 ± 0.4$^b$ | 3.89 ± 1.11$^a$ |
| 22:6 n-3(DHA) | 4.42 ± 1.29$^c$ | 4.50 ± 1.48$^c$ | 3.31 ± 1.37d | 5.72 ± 1.85$^b$ | 7.27 ± 1.89$^a$ |

Values represent mean ± SD (n = 3), different superscripts indicate significant difference from each other in groups, p < 0.01

Because fatty acid status of individuals is reported in a variety of ways it was important to compare the fatty acid spectrum in a dried blood spot with standard ways of reporting the fatty acids in blood. These included whole blood extract, plasma phospholipids, and red blood cell fatty acids. In addition, fatty acid groupings such as EPA+DHA (omega 3 index) in each of these blood fractions were compared with similar groupings found in dried blood spots.

The results here demonstrate that there is a high correlation between capillary dried blood spots fatty acid composition and corresponding fatty acid values found in the standard blood fractions (Table 11) and that these could be expressed as simple equations (see FIGS. 4 to 7).

TABLE 11

Correlation for fatty acid composition between capillary dried blood spot and conventional assays

| Capillary dried blood spot fatty acids | Corresponding fatty acids in venous blood fractions | | | |
|---|---|---|---|---|
| | Whole blood Total lipid | Plasma Total lipid | Plasma Phospholipid | Red Blood Cell Phospholipid |
| 16:0 | 0.961** | 0.962** | 0.771** | 0.626** |
| 18:0 | 0.938** | 0.843** | 0.551** | 0.7** |
| 16:1 n-7 | 0.946** | 0.878** | 0.623** | 0.511* |
| 18:1 n-9 | 0.982** | 0.971** | 0.463* | 0.674** |
| 18:2 n-6 (LA) | 0.991** | 0.854** | 0.896** | 0.824** |
| 18:3 n-3 (ALA) | 0.951** | 0.927** | 0.578** | 0.441* |
| 20:4 n-6 (AA) | 0.993** | 0.85** | 0.693** | 0.754** |
| 20:5 n-3(EPA) | 0.998** | 0.985** | 0.988** | 0.973** |
| 22:4 n-6 | 0.980** | 0.587** | 0.436* | 0.889** |

TABLE 11-continued

Correlation for fatty acid composition between capillary dried blood spot and conventional assays

| Capillary dried blood spot fatty acids | Corresponding fatty acids in venous blood fractions | | | |
|---|---|---|---|---|
| | Whole blood Total lipid | Plasma Total lipid | Plasma Phospholipid | Red Blood Cell Phospholipid |
| 22:5 n-3 (DPA) | 0.915** | 0.878** | 0.838** | 0.847** |
| 22:6 n-3(DHA) | 0.996** | 0.976** | 0.964** | 0.971** |

*p < 0.001
**p < 0.0001

Example 6

Effect of Storage Temperature on Fatty Acid Stability

The influence of storage temperature on the stability of fatty acids in a dried blood spot was tested. Blood was spotted onto Whatman silica gel chromatography papers which were impregnated with 2 mg/ml BHT and 5 mg/ml EDTA and dried in air for 5 hours. The dried blood spot samples were stored at −20° C., 4° C. and room temperature (19-23° C.) in zip-lock aluminium foil bags in the presence of desiccant. The fatty acid composition of the dried blood spot samples were analysed as described above after 5 hours, 2 weeks and 4 weeks. The results are shown below in Table 12

In general, there was no significant difference in the fatty acid composition among the dried blood spot samples stored at −20° C., 4° C. and room temperature (19-23° C.) over 4 weeks storage.

TABLE 12

Fatty acid composition of dried blood spots on silica gel loaded paper stored at different temperatures over 4 weeks

| | | After drying | −20° C. | | /35 4° C. | | RT (19-23° C.) | |
|---|---|---|---|---|---|---|---|---|
| Fatty acids[1] | Original[2] | (5 hrs) | 2 weeks | 4 weeks | 2 weeks | 4 weeks | 2 weeks | 4 weeks |
| 16:0 | 22.48 ± 0.22 | 22.55 ± 0.14 | 22.63 ± 0.2 | 22.68 ± 0.15 | 22.65 ± 0.18 | 22.84 ± 0.19 | 22.75 ± 0.27 | 22.92 ± 0.24 |
| 18:0 | 13.12 ± 0.18 | 13.19 ± 0.2 | 13.30 ± 0.17 | 13.41 ± 0.11 | 13.27 ± 0.08 | 13.39 ± 0.1 | 13.34 ± 0.07 | 13.42 ± 0.19 |
| 18:1 n-9 | 18.48 ± 0.07 | 18.52 ± 0.08 | 18.51 ± 0.15 | 18.75 ± 0.06 | 18.73 ± 0.05 | 18.86 ± 0.07 | 18.60 ± 0.09 | 18.94 ± 0.14 |

TABLE 12-continued

Fatty acid composition of dried blood spots on silica gel loaded paper stored at different temperatures over 4 weeks

| Fatty acids[1] | Original[2] | After drying (5 hrs) | −20° C. 2 weeks | −20° C. 4 weeks | /35 4° C. 2 weeks | /35 4° C. 4 weeks | RT (19-23° C.) 2 weeks | RT (19-23° C.) 4 weeks |
|---|---|---|---|---|---|---|---|---|
| 18:2 n-6 | 19.66 ± 0.08 | 19.62 ± 0.12 | 19.64 ± 0.12 | 19.56 ± 0.09 | 19.60 ± 0.06 | 19.57 ± 0.13 | 19.65 ± 0.16 | 19.52 ± 0.06 |
| 18:3 n-3 | 0.5 ± 0.01 | 0.49 ± 0.01 | 0.50 ± 0.02 | 0.49 ± 0.01 | 0.49 ± 0.01 | 0.48 ± 0.01 | 0.50 ± 0.01 | 0.49 ± 0.01 |
| 20:4 n-6 | 7.81 ± 0.09 | 7.77 ± 0.07 | 7.65 ± 0.06 | 7.58 ± 0.07 | 7.60 ± 0.02 | 7.48 ± 0.06 | 7.65 ± 0.08 | 7.52 ± 0.07 |
| 20:5 n-3 | 6.75 ± 0.08 | 6.70 ± 0.06 | 6.65 ± 0.07 | 6.58 ± 0.07 | 6.59 ± 0.09 | 6.40 ± 0.07 | 6.54 ± 0.09 | 6.38 ± 0.07 |
| 22:4 n-6 | 0.49 ± 0.01 | 0.50 ± 0.02 | 0.49 ± 0.02 | 0.48 ± 0.01 | 0.49 ± 0.01 | 0.49 ± 0.01 | 0.48 ± 0.02 | 0.49 ± 0.01 |
| 22:5 n-3 | 3.65 ± 0.03 | 3.64 ± 0.02 | 3.66 ± 0.06 | 3.60 ± 0.04 | 3.65 ± 0.02 | 3.61 ± 0.05 | 3.60 ± 0.05 | 3.57 ± 0.05 |
| 22:6 n-3 | 7.06 ± 0.05 | 7.02 ± 0.1 | 6.97 ± 0.06 | 6.87 ± 0.07 | 6.93 ± 0.07 | 6.78 ± 0.06 | 6.89 ± 0.09 | 6.75 ± 0.12 |

[1]Values represent mean ± SD (n = 3), no significant difference from each other in groups, p < 0.01.
[2]"Original" means the fatty acid composition obtained from direct transmethylation of 50 μl fresh blood Example 7

Effect of Shelf Life on the Solid Medium

Figure 8:
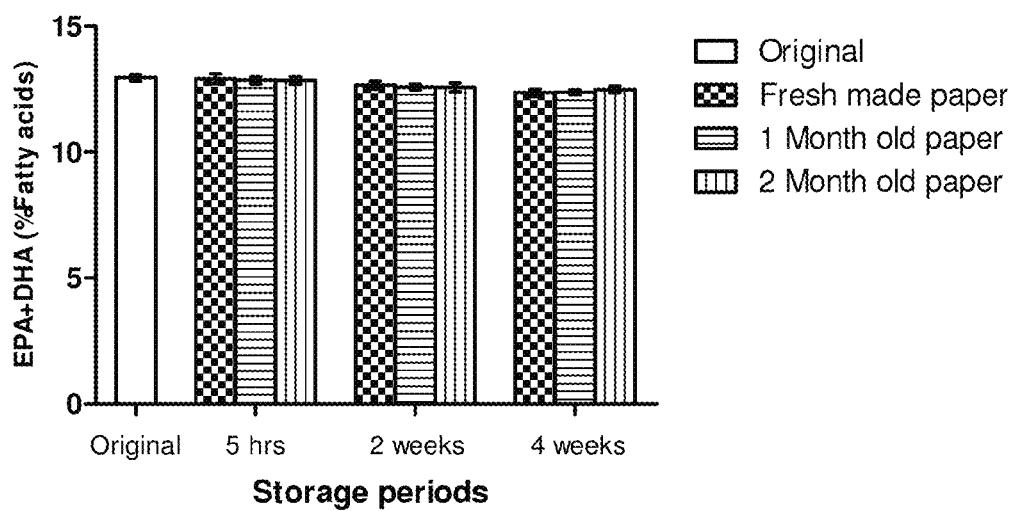
FIG. 8 shows the fatty acid composition of blood spots on fresh made and pre-made paper stored at room temperature over 4 weeks. Values represent mean±SD (n=3), no significant difference from each other, p<0.01. "Original" means the fatty acid composition obtained from direct transmethylation of 50 µl fresh blood

The influence of storage period on the stability of the solid medium was tested. Whatman silica gel chromatography papers were impregnated with 2 mg/ml BHT and 5 mg/ml EDTA and stored for 1 month and 2 months prior to use. Blood was spotted on both stored papers as well as papers treated with a freshly made protectant solution (2 mg/ml BHT+5 mg/ml EDTA). Blood spots were dried in air for 5 hours and then stored at room temperature (19-23° C.) in zip-lock aluminium foil bags with the presence of desiccant. The fatty acid composition of the dried blood spot samples were analysed as described above after 5 hours, 2 weeks and 4 weeks. The results are shown below in Table 13 and in FIG. 8.

TABLE 13

Fatty acid composition of blood spots on freshly prepared or prior prepared silica gel loaded paper stored at room temperatures over 4 weeks

| Fatty acids[1] | Original[2] | Fresh made paper 5 hrs | Fresh made paper 2 weeks | Fresh made paper 4 weeks | 1 month old paper 5 hrs |
|---|---|---|---|---|---|
| 16:0 | 24.70 ± 0.24 | 24.77 ± 0.13 | 24.85 ± 0.14 | 25.01 ± 0.23 | 24.90 ± 0.12 |
| 18:0 | 13.07 ± 0.13 | 13.12 ± 0.09 | 13.02 ± 0.14 | 13.23 ± 0.19 | 13.15 ± 0.1 |
| 18:1 n-9 | 19.25 ± 0.12 | 19.20 ± 0.22 | 19.59 ± 0.13 | 19.86 ± 0.18 | 19.21 ± 0.06 |
| 18:2 n-6 | 18.78 ± 0.09 | 18.74 ± 0.14 | 18.73 ± 0.09 | 18.49 ± 0.14 | 18.68 ± 0.07 |
| 18:3 n-3 | 0.53 ± 0.01 | 0.53 ± 0.01 | 0.48 ± 0.01 | 0.54 ± 0.01 | 0.52 ± 0.02 |
| 20:4 n-6 | 7.17 ± 0.09 | 7.22 ± 0.11 | 7.19 ± 0.03 | 7.10 ± 0.05 | 7.17 ± 0.08 |
| 20:5 n-3 | 6.33 ± 0.06 | 6.30 ± 0.08 | 6.15 ± 0.11 | 6.03 ± 0.07 | 6.31 ± 0.05 |
| 22:4 n-6 | 0.58 ± 0.02 | 0.57 ± 0.01 | 0.54 ± 0.02 | 0.54 ± 0.01 | 0.54 ± 0.01 |
| 22:5 n-3 | 2.96 ± 0.03 | 2.94 ± 0.03 | 2.94 ± 0.03 | 2.88 ± 0.05 | 2.98 ± 0.02 |
| 22:6 n-3 | 6.63 ± 0.05 | 6.61 ± 0.1 | 6.51 ± 0.04 | 6.32 ± 0.07 | 6.54 ± 0.09 |

| Fatty acids[1] | 1 month old paper 2 weeks | 1 month old paper 4 weeks | 2 month old paper 5 hrs | 2 month old paper 2 weeks | 2 month old paper 4 weeks |
|---|---|---|---|---|---|
| 16:0 | 24.94 ± 0.17 | 25.11 ± 0.15 | 24.84 ± 0.16 | 24.86 ± 0.23 | 24.95 ± 0.17 |
| 18:0 | 13.11 ± 0.16 | 13.19 ± 0.09 | 13.18 ± 0.13 | 13.16 ± 0.18 | 13.21 ± 0.15 |
| 18:1 n-9 | 19.64 ± 0.05 | 19.89 ± 0.18 | 19.30 ± 0.18 | 19.66 ± 0.13 | 19.80 ± 0.14 |
| 18:2 n-6 | 18.61 ± 0.12 | 18.37 ± 0.08 | 18.62 ± 0.08 | 18.59 ± 0.19 | 18.53 ± 0.1 |
| 18:3 n-3 | 0.49 ± 0.01 | 0.53 ± 0.01 | 0.51 ± 0.01 | 0.49 ± 0.01 | 0.50 ± 0.01 |
| 20:4 n-6 | 7.14 ± 0.05 | 7.08 ± 0.05 | 7.17 ± 0.06 | 7.15 ± 0.08 | 7.08 ± 0.05 |
| 20:5 n-3 | 6.12 ± 0.06 | 6.07 ± 0.05 | 6.29 ± 0.07 | 6.13 ± 0.08 | 6.08 ± 0.09 |
| 22:4 n-6 | 0.54 ± 0.02 | 0.57 ± 0.01 | 0.55 ± 0.01 | 0.56 ± 0.01 | 0.57 ± 0.02 |
| 22:5 n-3 | 2.95 ± 0.02 | 2.89 ± 0.04 | 2.99 ± 0.03 | 2.96 ± 0.04 | 2.88 ± 0.06 |
| 22:6 n-3 | 6.46 ± 0.05 | 6.30 ± 0.05 | 6.55 ± 0.08 | 6.44 ± 0.09 | 6.40 ± 0.05 |

[1]Values represent mean ± SD (n = 3), no significant difference from each other in groups, p < 0.01.
[2]"Original" means the fatty acid composition obtained from direct transmethylation of 50 μl fresh blood In general, the results demonstrated that solid media which were pre-made 2 months prior to use have the same efficacy in stabilising LCPUFA as freshly prepared solid media. Whilst shelf life was investigated for 2 months in this example, the results clearly indicate the possibility that pre-made solid media may have a longer shelf life.

REFERENCES

1. W. C. Tu, et al. 2010. Omega-3 long chain fatty acid synthesis is regulated more by substrate levels than gene expression. *Prostaglandins, Leukotrienes and Essential Fatty Acids*, 83, 61-68.
2. Min, Y. J., et al. 2011. Effect of storage temperature and length on fatty acid composition of fingertip blood collected on filter paper. *Prostaglandins, Leukotrienes and Essential Fatty Acids*, 84, 13-18.

The claims defining the invention are as follows:

1. A method for stabilising fatty acids, comprising
    applying the fatty acids, or a sample comprising the fatty acids, to a solid medium
        comprising
            a solid matrix,
            at least one chelating agent and
            at least one antioxidant,
                wherein the solid matrix comprises less than about 2 μg/cm$^2$ of one or more contaminants.
2. The method of claim 1, wherein the solid matrix comprises less than about 1 μg/cm$^2$ of said one or more contaminants.
3. The method of claim 2, wherein the solid matrix comprises less than about 0.5 μg/cm$^2$ of said one or more contaminants.
4. The method of claim 1, wherein the contaminants are saturated fatty acids.
5. The method of claim 1, wherein the solid matrix is selected from the group consisting of: paper, a glass-based matrix, a paper-based matrix, a cellulose-based matrix, hydrophilic polymers, polytetrafluoroethylene, fibreglass and porous ceramics.
6. The method of claim 1, wherein the solid matrix is selected from the group consisting of: paper, a paper-based matrix and a glass-based matrix.
7. The method of claim 1, wherein the solid matrix is silica gel-loaded paper.
8. The method of claim 1, wherein the solid matrix is a glass microfiber filter.
9. The method of claim 1, wherein the sample is a biological sample.
10. The method of claim 9, wherein the biological sample is a bodily fluid.
11. The method of claim 10, wherein the bodily fluid is selected from the group consisting of: blood, saliva, breast milk, urine, semen, blood plasma and serum.
12. The method of claim 11, wherein the bodily fluid is blood.
13. The method of claim 1, wherein the at least one chelating agent is ethylenediamine-tetraacetic acid, ascorbic acid, or salts thereof, or citric acid, or salts thereof.
14. The method of claim 1, wherein the at least one antioxidant is butylated hydroxytoluene, butylated hydroxyanisole or t-butylhydroquinone.
15. The method of claim 1, wherein the chelating agent is ascorbic acid and/or ethylenediamine-tetraacetic acid and the antioxidant is butylated hydroxytoluene.
16. The method of claim 1, wherein the fatty acids are unsaturated fatty acids.
17. The method of claim 1, wherein the solid medium is in the form of a strip.
18. The method of claim 17, wherein the strip has dimensions of about 1 cm×3 cm.
19. The method of claim 1, wherein the antioxidant(s) are present on the solid medium in an amount about 0.01 mg to about 1 mg.
20. The method of claim 1, wherein the chelating agent(s) are present on the solid medium in an amount about 0.01 mg to about 1 mg.
21. A method for stabilising fatty acids according to claim 1, comprising
    applying the fatty acids, or a fluid comprising the fatty acids, to a solid medium
        comprising
            a glass microfiber filter or silica gel-loaded paper,
            ethylenediamine-tetraacetic acid and/or ascorbic acid and
            butylated hydroxytoluene.
22. A method for determining fatty acid composition of a sample comprising fatty acids, the method comprising:
    (a) applying the sample to a solid medium comprising
        a solid matrix,
        at least one chelating agent and
        at least one antioxidant,
            wherein the solid matrix comprises less than about 2 μg/cm$^2$ of one or more contaminants, such that the sample is sorbed to the solid matrix;
    (b) determining the fatty acid composition of the sample sorbed to the solid matrix.
23. The method of claim 22, wherein the solid matrix comprises less than about 1 μg/cm$^2$ of the one or more contaminants.
24. The method of claim 22, wherein the solid matrix comprises less than about 0.5 μg/cm$^2$ of the one or more contaminants.
25. The method of claim 22, wherein the one or more contaminants are saturated fatty acids.
26. The method of claim 22, wherein the solid matrix is selected from the group consisting of: paper, a glass-based matrix, a paper-based matrix, a cellulose-based matrix, hydrophilic polymers, polytetrafluoroethylene, fibreglass and porous ceramics.
27. The method of claim 22, wherein the solid matrix is selected from the group consisting of: paper, a paper-based matrix and a glass-based matrix.
28. The method of claim 22, wherein the solid matrix is silica gel-loaded paper.
29. The method of claim 22, wherein the solid matrix is a glass microfiber filter.
30. The method of claim 22, wherein the sample is a biological sample.
31. The method of claim 30, wherein the biological sample is a bodily fluid.
32. The method of claim 31, wherein the bodily fluid is selected from the group consisting of: blood, saliva, breast milk, urine, semen, blood plasma and serum.
33. The method of claim 32, wherein the bodily fluid is blood.
34. The method of claim 22, wherein the at least one chelating agent is ethylenediamine-tetraacetic acid, ascorbic acid, or salts thereof, or citric acid, or salts thereof.
35. The method of claim 22, wherein the at least one antioxidant is butylated hydroxytoluene, butylated hydroxyanisole or t-butylhydroquinone.

36. The method of claim 22, wherein the chelating agent is ascorbic acid and/or ethylenediamine-tetraacetic acid and the antioxidant is butylated hydroxytoluene.

37. The method of claim 22, wherein (b) comprises:
(i) extracting at least a portion of the sample sorbed to the solid matrix to provide an extract comprising derivatised fatty acids;
(ii) determining the fatty acid composition of the sample based on amounts of the derivatised fatty acids.

38. A solid medium said medium comprising
a solid matrix,
at least one chelating agent and
at least one antioxidant,
wherein the solid matrix comprises less than about 2 µg/cm$^2$ of one or more contaminants.

39. The solid medium of claim 38, wherein the solid matrix comprises less than about 1 µg/cm$^2$ of the one or more contaminants.

40. The solid medium of claim 39, wherein the solid matrix comprises less than about 0.5 µg/cm$^2$ of the one or more contaminants.

41. The solid medium of claim 38, wherein the one or more contaminants are saturated fatty acids.

42. The solid medium of claim 38, wherein the solid matrix is selected from the group consisting of: paper, a glass-based matrix, a paper-based matrix, a cellulose-based matrix, hydrophilic polymers, polytetrafluoroethylene, fibreglass and porous ceramics.

43. The solid medium of claim 38, wherein the solid matrix is selected from the group consisting of: paper, a paper-based matrix and a glass-based matrix.

44. The solid medium of claim 38, wherein the solid matrix is silica gel-loaded paper.

45. The solid medium of claim 38, wherein the solid matrix is a glass microfiber filter.

46. The solid medium of claim 38, wherein the at least one chelating agent is ethylenediamine-tetraacetic acid, ascorbic acid, or salts thereof, or citric acid, or salts thereof.

47. The solid medium of claim 38, wherein the at least one antioxidant is butylated hydroxytoluene, butylated hydroxyanisole or t-butylhydroquinone.

48. The solid medium of claim 38, wherein the chelating agent is ascorbic acid and/or ethylenediamine-tetraacetic acid and the antioxidant is butylated hydroxytoluene.

49. The solid medium of claim 38, wherein the solid medium is in the form of a strip.

50. The solid medium of claim 49, wherein the strip has dimensions of about 1 cm×3 cm.

51. The solid medium of claim 38, wherein the antioxidant(s) are present on the solid medium in an amount about 0.01 mg to about 1 mg.

52. The solid medium of claim 38, wherein the chelating agent(s) are present on the solid medium in an amount about 0.01 mg to about 1 mg.

53. A solid medium according to claim 38, said medium comprising
a glass microfiber filter or silica gel-loaded paper,
ethylenediamine-tetraacetic acid and/or ascorbic acid and
butylated hydroxytoluene.

54. A method for preparing a solid medium comprising a solid matrix, at least one chelating agent and at least one antioxidant, comprising:
providing a solid medium comprising the solid matrix and
applying to the solid medium the at least one chelating agent and the at least one antioxidant,
wherein the solid matrix comprises less than about 2 µg/cm$^2$ of one or more contaminants.

55. The method of claim 54, wherein the solid matrix comprises less than about 1 µg/cm$^2$ of the one or more contaminants.

56. The method of claim 55, wherein the solid matrix comprises less than about 0.5 µg/cm$^2$ of the one or more contaminants.

57. The method of claim 54, wherein the one or more contaminants are saturated fatty acids.

58. The method of claim 54, wherein the solid matrix is selected from the group consisting of: paper, a glass-based matrix, a paper-based matrix, a cellulose-based matrix, hydrophilic polymers, polytetrafluoroethylene, fibreglass and porous ceramics.

59. The method of claim 54, wherein the solid matrix is selected from the group consisting of: paper, a paper-based matrix and a glass-based matrix.

60. The method of claim 54, wherein the solid matrix is silica gel-loaded paper.

61. The method of claim 54, wherein the solid matrix is a glass microfiber filter.

62. The method of claim 54, wherein the at least one chelating agent is ethylenediamine-tetraacetic acid, ascorbic acid, or salts thereof, or citric acid, or salts thereof.

63. The method of claim 54, wherein the at least one antioxidant is butylated hydroxytoluene, butylated hydroxyanisole or t-butylhydroquinone.

64. The method of claim 54, wherein the chelating agent is ascorbic acid and/or ethylenediamine-tetraacetic acid and the antioxidant is butylated hydroxytoluene.

65. The method of claim 54, wherein the at least one antioxidant and the at least one chelating agent are applied to the solid medium in the form of a single solution or separate solutions, one solution comprising the at least one antioxidant and one solution comprising the at least one chelating agent.

66. The method of claim 65, wherein the solution(s) comprise alcohol and water.

67. The method of claim 65, wherein the concentration of the at least one antioxidant in the solution is about 0.1 mg/mL to about 10 mg/mL.

68. The method of claim 65, wherein the concentration of the at least one chelating agent in the solution is about 1 mg/mL to about 10 mg/mL.

69. The method of claim 54, wherein the solid medium is in the form of a strip.

70. The method of claim 65, wherein the amount of solution applied to the strip is from about 1 to 500 µL.

71. The method of claim 69, wherein the strip has dimensions of about 1 cm×3 cm.

72. A kit comprising the solid medium of claim 38.

73. The kit according to claim 72, further comprising a sharp object for obtaining a sample comprising fatty acids from a subject.

74. The kit of claim 73, wherein the sample is blood.

* * * * *